US009014801B2

(12) United States Patent
Perez et al.

(10) Patent No.: US 9,014,801 B2
(45) Date of Patent: Apr. 21, 2015

(54) ELECTROMAGNETIC FIELD THERAPY DELAYS CELLULAR SENESCENCE AND DEATH BY ENHANCEMENT OF THE HEAT SHOCK RESPONSE

(75) Inventors: Felipe Pablo Perez, Oak Park, IL (US); Donald A. Jurivich, La Grange, IL (US); Jorge Javier Morisaki, Oak Forest, IL (US); Ximing Zhou, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1260 days.

(21) Appl. No.: 12/407,616

(22) Filed: Mar. 19, 2009

(65) Prior Publication Data

US 2009/0276019 A1  Nov. 5, 2009

Related U.S. Application Data

(60) Provisional application No. 61/037,782, filed on Mar. 19, 2008, provisional application No. 61/119,533, filed on Dec. 3, 2008.

(51) Int. Cl.
| | |
|---|---|
| *A61N 1/02* | (2006.01) |
| *C12N 13/00* | (2006.01) |
| *A61N 1/40* | (2006.01) |
| *A61N 5/02* | (2006.01) |

(52) U.S. Cl.
CPC ............... *C12N 13/00* (2013.01); *A61N 1/403* (2013.01); *A61N 5/02* (2013.01)

(58) Field of Classification Search
USPC ............................................................ 607/2
See application file for complete search history.

(56) References Cited

U.S. PATENT DOCUMENTS

| | | | |
|---|---|---|---|
| 6,919,207 B2 | 7/2005 | Goodman et al. | |
| 7,367,988 B1 * | 5/2008 | Litovitz | ....................... 607/106 |
| 2007/0238682 A1 | 10/2007 | Nudler et al. | |

OTHER PUBLICATIONS

Arendash, et al., "Electromagnetic Field Treatment Protects Against and Reverses Cognitive Impairment in Alzheimer's Disease Mice," Journal of Alzheimer's Disease 19, 2010, pp. 191-210.
Perez, Felipe P. et al., "Electromagnetic Field Therapy Delays Cellular Senescence and Death by Enhancement of the Heath Shock Response," Experimental Gerontology, Jan. 2008, pp. 307-316, Issue 43, ScienceDirect.
Perez, Felipe P. et al., "Engineered Repeated Electromagnetic Field Shock Therapy for Cellular Senescence and Age-Related Diseases," Rejuvenation Research, 2008, pp. 1049-1057, vol. 11, No. 6, Mary Ann Liebert, Inc.

* cited by examiner

*Primary Examiner* — Joseph Dietrich
(74) *Attorney, Agent, or Firm* — Banner & Witcoff, Ltd.

(57) ABSTRACT

Disclosed herein is a method comprising repetitive electromagnetic field shock to at least one living cell, wherein the repetitive electromagnetic field shock improves HSF1 and/or HSR function, and producing delaying and reversal of aging and age related diseases. Also disclosed herein is an apparatus adapted to deliver repetitive electromagnetic field shock to at least one living cell, wherein the repetitive electromagnetic field shock improves HSF1 and HSR function.

23 Claims, 13 Drawing Sheets

ELECTROMAGNETIC FIELD THERAPY DELAYS CELLULAR SENESCENCE AND DEATH BY ENHANCEMENT OF THE HEAT SHOCK RESPONSE

CROSS-REFERENCE TO RELATED APPLICATIONS

This application claims priority to U.S. Provisional Application Ser. No. 61/037,782, filed Mar. 19, 2008, and entitled "Repeated Electromagnetic Field Shock (REMFS) Delays and Reverses Cellular Senescence and Mortality by Preconditioning of the HSF1/HSR Pathway," and U.S. Provisional Application Ser. No. 61/119,533, filed Dec. 3, 2008, and entitled "Engineered Repeated Electromagnetic Fields Shock (REMFS) Therapy for Cellular Senescence and Age-Related Disease," both of which are hereby incorporated herein in their entireties.

FIELD OF THE INVENTION

This invention relates generally to electromagnetic field therapy to delay cellular senescence and death by enhancement of the heat shock response.

BACKGROUND

Hormesis occurs when otherwise damaging stimuli produce beneficial effects after low dose applications. (Calabrese, E. J., and Baldwin, L. A., 1998. Hormesis as a biological hypothesis. Environ Health Perspect 106 Suppl 1357-36; Rattan, S. I., 2001, Applying hormesis in aging research and therapy. Hum Exp Toxicol 20(6), 281-285; discussion 293-284.) Several hormetic stimuli appear to promote life span extension. (Cypser, J. R. and Johnson, T. E., 2002. Multiple stressors in *Caenorhabditis elegans* induce stress hormesis and extended longevity. J. Gerontol A Biol Sci Med Sci 57(3): B109-114.) UV and ionizing radiation, temperature, hypergravity, and dietary restriction extend life span in diverse species. (Rattan, S. I., 2004a. Aging intervention, prevention, and therapy through hormesis. J Gerontol A Biol Sci Med Sci 59(7), 705-709.) Temperature modulation such as heat shock can promote hormetic effects as shown in other studies. (Verbeke, P., Clark, B. F., and Rattan, S. I., 2000. Modulating cellular aging in vitro: hormetic effects of repeated mild heat stress on protein oxidation and glycation. Exp Gerontol 35(6-7), 787-794.) Repeated mild heat-shock (RMHS) generates anti-aging hormetic effects on human fibroblasts undergoing in vitro senescence. (Fonager, J., Beedholm, R., Clark, B. F., and Rattan, S. I., 2002. Mild stress-induced stimulation of heat-shock protein synthesis and improved functional ability of human fibroblasts undergoing aging in vitro. Exp Gerontol 37(10-11), 1223-1228.) When in vitro senescence is delayed, progressive cell enlargement is retarded, abnormal proteins are prevented, reduced glutathione increases, and age-dependent glycocylation end products decline. (Rattan, S. I., 1998. Repeated mild heat shock delays ageing in cultured human skin fibroblasts. Biochem Mol Biol Int 45(4), 753-759; Verbeke, P., Clark, B. F., and Rattan, S. I., 2001a. Reduced levels of oxidized and glycoxidized proteins in human fibroblasts exposed to repeated mild heat shock during serial passaging in vitro. Free Radic Biol Med 31(12), 1593-1602; Verbeke, P., Deries, M., Clark, B. F., and Rattan, S. I., 2002. Hormetic action of mild heat stress decreases the inducibility of protein oxidation and glycoxidation in human fibroblasts. Biogerontology 3(1-2), 117-120.) Cellular anti-aging effects include maintenance of youthful morphology, increased levels of various heat shock proteins (Hsps), increased proteasomal activities, increased antioxidative abilities, and increased resistance to damage by ethanol, hydrogen peroxide, and UV-A irradiation (Parsons, Pa. The limit to human longevity: an approach through a stress theory of ageing. Mech Ageing Dev. 1996; 87: 211-8; Caratero, A, Courtade, M, Bonnet, L, Planel, H and Caratero, C. Effect of a continuous gamma irradiation at a very low dose on the life span of mice. Gerontology. 1998; 44: 272-6; Yukawa, 0, Nakajima, T, Yukawa, M, Ozawa, T and Yamada, T. Induction of radical scavenging ability and protection against radiation-induced damage to microsomal membranes following low-dose irradiation. Int J Radiat Biol. 1999; 75: 1189-99; Miura, Y, Abe, K, Urano, S, Furuse, T, Noda, Y, Tatsumi, K and Suzuki, S. Adaptive response and the influence of ageing: effects of low-dose irradiation on cell growth of cultured glial cells. Int J Radiat Biol. 2002; 78: 913-21; Khazaeli, A A, Tatar, M, Pletcher, S D and Curtsinger, J W. Heat-induced longevity extension in *Drosophila*. I. Heat treatment, mortality, and thermotolerance. J Gerontol A Biol Sci Med Sci. 1997; 52: B48-52). How these hormetic effects are achieved remain to be fully elucidated.

Many hormetic effects appear to be mediated, in part, by various components of the heat shock response (HSR). (Rattan, S. I., 2004b. Mechanisms of hormesis through mild heat stress on human cells. Ann N Y Acad Sci 1019554-558; Rattan, S. I., 2007. Hormesis in ageing. Ageing Res Rev August 31 (e pub)) As a primordial intracellular defense mechanism against stressful conditions, preferential transcription and translation of heat shock messenger RNA leading to short term hsp accumulation prepare cells for lethal and damaging results. (Hayes, S. A., and Dice, J. F., 1996. Roles of molecular chaperones in protein degradation. J Cell Biol 132(3), 225-258; Jindal, S., 1996. Heat shock proteins: applications in health and disease. Trends Biotechnol 14(1), 17-20; Udelsman, R., Blake, M. J., Stagg, C. A., and Holbrook, N. J., 1994. Endocrine control of stress-induced heat shock protein 70 expression in vivo. Surgery 115(5), 611-616.) Optimal HSR is beneficial for cell survival; whereas, inefficient and altered HSR results can result in abnormal growth, development, aging and apoptosis. (Rattan, S. I., and Derventzi, A., 1991. Altered cellular responsiveness during ageing. Bioessays 13(11), 601-606; Soti, C., and Csermely, P., 2000. Molecular chaperones and the aging process. Biogerontology 1(3), 225-233.) It appears that HSR declines during senescence due to a variety of factors, but mostly attributable to a decrease in Heat Shock Factor 1 (HSF1)-DNA binding. (Udelsman, R., Blake, M. J., Stagg, C. A., and Holbrook, N. J., 1994. Endocrine control of stress-induced heat shock protein 70 expression in vivo. Surgery 115(5), 611-616.) It is believed that the transcription factor HSF1 centrally modulates HSR. It is believed that in the absence of stress, HSF1 rests in an un-activated state and is constrained by self-folding and HSP90 juxtaposed as a molecular brake. It has been reported that HSP90 prevents HSF1-DNA binding. (Satyal, S. H., Chen, D., Fox, S. G., Kramer, J. M., and Morimoto, R. I., 1998. Negative regulation of the heat shock transcriptional response by HSBP1. Genes Dev 12(13), 1962-1974; Zou, J., Guo, Y., Guettouche, T., Smith, D. F., and Voellmy, R., 1998. Repression of heat shock transcription factor HSF1 activation by HSP90 (HSP90 complex) that forms a stress-sensitive complex with HSF1. Cell 94(4), 471-480.) Different forms of stress can cause HSF1 to unfold, become hyper-phosphorylated, and form homo-trimers that acquire DNA binding capability. It has been reported that a possible cause of disrupted HSF1-Hsp90 complexes during stress is the accumulation of denatured polypeptides that attract Hsp90 from HSF1. (Bharadwaj, S., Ali, A., and Ovsenek, N., 1999. Multiple components of the HSP90 chaperone complex function in regulation of heat shock factor 1 in vivo. Mol Cell Biol 19(12), 8033-8041; Guo, Y., Guettouche, T., Fenna, M., Boellmann, F., Pratt, W. B., Toft, D. O., Smith, D. F., and Voellmy, R., 2001. Evidence for a mechanism of repression of heat shock factor 1 transcriptional activity by a multichaperone complex. J Biol Chem 276(49), 45791-45799; Zou, J., Guo, Y., Guettouche, T., Smith, D. F., and Voellmy, R., 1998. Repression of heat shock transcription factor HSF1 activation by HSP90 (HSP90 complex) that forms a stress-sensitive complex with HSF1. Cell 94(4), 471-480.) It has been reported that during stress recovery, HSF1 trimers reassociate with Hsp90 complexes. (Satyal, S. H., Chen, D., Fox, S. G., Kramer, J. M., and Morimoto, R. I., 1998. Negative regulation of the heat shock transcriptional response by HSBP1. Genes Dev 12(13), 1962-1974; Zou, J., Guo, Y., Guettouche, T., Smith, D. F., and Voellmy, R., 1998. Repression of heat shock transcription factor HSF1 activation by HSP90 (HSP90) that forms a stress-sensitive complex with HSF1. Cell 94(4), 471-480.

At the organism level anti-aging and life-prolonging effects of heat shock have been reported for *Drosophila* (Khazaeli, A. A., Tatar, M., Pletcher, S. D., and Curtsinger, J. W., 1997. Heat-induced longevity extension if *Drosophila*. I. Heat treatment, mortality, and thermotolerance, J Gerontol A Biol Sci Med Sci 52(1), B48-52; Hercus, M. J., Loeschcke, V., and Rattan, S. I., 2003. Lifespan extension of *Drosophila malanogaster* through hormesis by repeated mild heat stress. Biogeront 44(3), 149-156; Sorensen, J. G., Kristensen, T. N., Kristensen, K. V., Loeschcke, V., 2007. Sex specific effects of heat induced hormesis in Hsf-deficient *Drosophila melanogaster*. Exp Gerontol 42(12), 1123-1129) and nematodes (Lithgow, G. J., 1996. Invertebrate gerontology: the age mutations of *Caenorhabditis elegans*. Bioessays 18(10), 809-815; Lithgow, G. J., White, T. M., Melov, S., and Johnson, T. E., 1995. Thermotolerance and extended life-span conferred by single-gene mutations and induced by thermal stress. Proc Natl Acad Sci USA 92(16), 7540-7544; Olsen, A., Vantipalli, M. C., Lithgow, G. J., 2006. Lifespan extension of *Caenorhabditis elegans* following repeated mild hormetic heat treatments. Biogerontology 7(4): 221-230). Attempts to reproduce anti-aging effects in large mammalian organs pose an interesting challenge due to unintended external heat damage.

There is a continuing need in the art to identify safe and effective ways to treat diseases and provide anti-aging and life-prolonging effects.

BRIEF SUMMARY OF THE INVENTION

Aspects of the invention relate to a method comprising repetitive electromagnetic field shock (REMFS) to at least one living cell, wherein the repetitive electromagnetic field shock improves HSF1 and/or HSR function. In accordance with exemplary methods, REMFS may act by a novel mechanism that does not directly activate the HSR. Novel methods disclosed herein can disrupt the HSF1-HSP90 complex. Such novel methods may be employed without causing protein damage as observed in prior art studies with EMF. Methods utilizing REMFS described herein can comprise any suitable protocol, including, but not limited, to about 5-30 minutes per day every day, every two days, or every three days, or twice a week, of about 50 MHz/0.5 W continuous radiation, and/or until cells reach cellular senescence.

Exemplary methods disclosed herein provide beneficial effects on aging processes of living cells. In accordance with certain methods, the application of the REMFS can extend the replicative lifespan of cells. In one embodiment, the REMFS may extend the replicative lifespan of cells that appeared to have reached their terminal lifespan before the application of the REMFS. In another embodiment, the REMFS may delay the average age-related enlargement and diversification of cells, and/or revert the cells to a more youthful phenotype.

Another aspect of the invention relates to an apparatus adapted to deliver repetitive electromagnetic field shock to at least one living cell, wherein the repetitive electromagnetic field shock improves HSF1 function. The REMFS can be delivered by an apparatus controlled by a computer that is programmed to deliver about 5-30 minutes per day every day, every two days, or every three days, or twice a week, of about 50 MHz/0.5 W continuous radiation, and/or until cells reach cellular senescence. The apparatus can be adapted to deliver the REMFS to the entire body of a patient and/or adapted to deliver the REMFS to a particular part of the body of patient.

These and other embodiments, which will be apparent to those of skill in the art upon reading the specification, provide the art with methods of treating diseases and populations of cells.

BRIEF DESCRIPTION OF THE DRAWINGS

Non-limiting embodiments will now be described with reference to the accompanying drawings.

FIGS. 1A and 1B show results from proliferating, IL2 stimulated T cells. FIG. 1A is a bar graph representation of LDH values released into cell culture media as measured by absorbance spectroscopy. FIG. 1B is a line graph of T lymphoblast mortality every 3 to 4 days as measured by Trypan blue exclusion. FIGS. 1C and 1D show both LDH release and Trypan blue exclusion for quiescent T cells that were maintained in fresh media over a 7 day period.

FIG. 2A shows results from an electrophoretic mobility shift assay (EMSA) carried out with whole cell extracts of T-lymphoblasts with or without EMF treatment. FIG. 2B is a bar graph that displays phosphoimaging data that measures the relative values of the HSF1-HSE complexes.

DETAILED DESCRIPTION OF THE INVENTION

Figure 1:
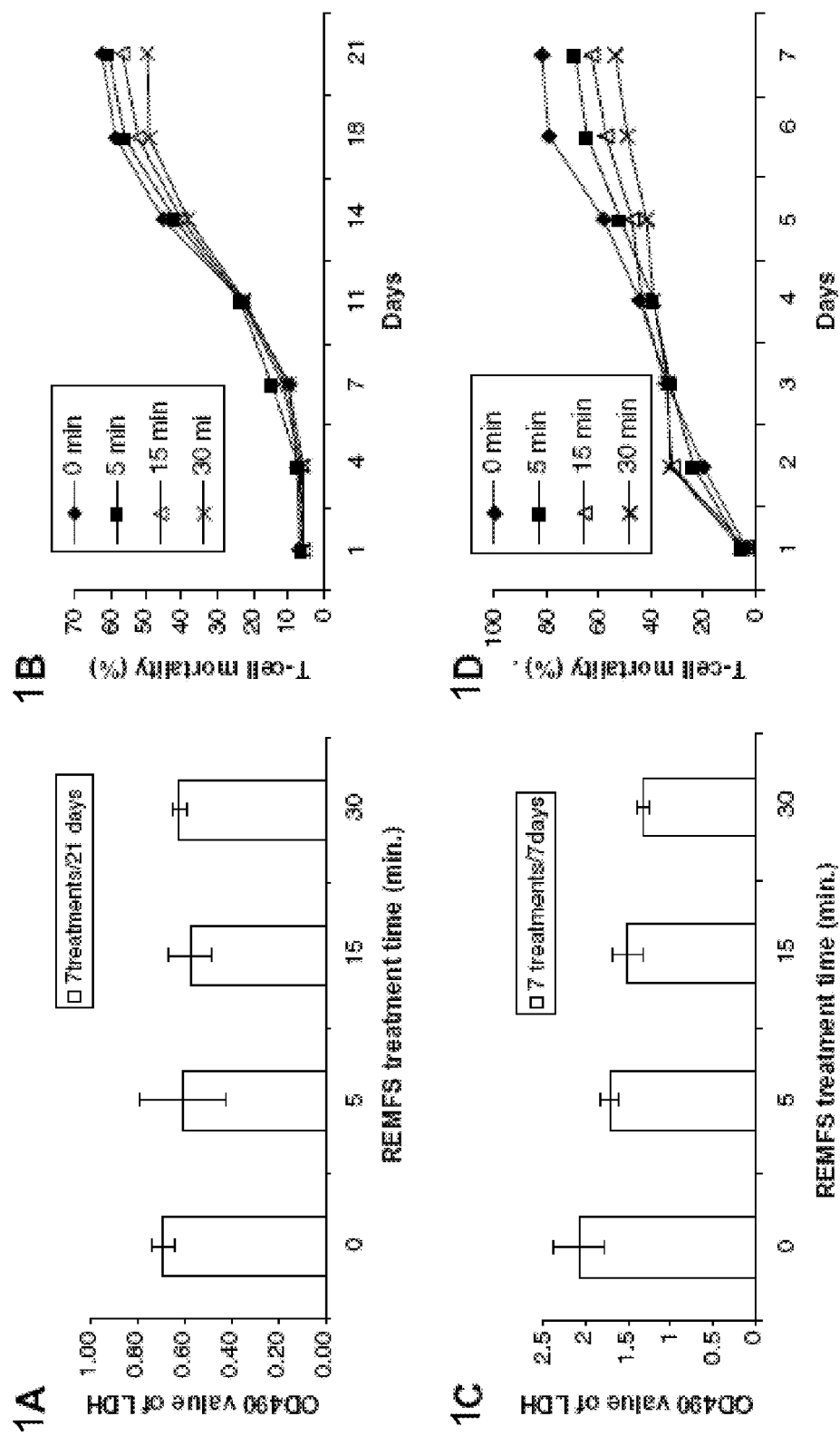
FIGS. 1A, 1B, 1C and 1D illustrate exemplary embodiments in which REMFS decreased T-lymphocyte mortality.

It has now been found that REMFS can achieve several biological effects that modify the aging process. As further described herein, REMFS can extend the total number of population doublings of mouse fibroblasts and contribute to youthful morphology of cells near their replicative lifespan. REMFS can also enhance cellular defenses of human T cells as reflected in lower cell mortality when compared to non-treated T cells. To determine the mechanism of REMFS-induced effects, analysis of the cellular heat shock response revealed Hsp90 release from the heat shock transcription factor (HSF1). Furthermore, REMFS increased HSF1 phosphorylation, enhanced HSF1-DNA binding, and improved HSP70 expression relative to non-REMFS treated cells. These results show that non-thermal REMFS activates an anti-aging hormetic effect as well as reduces cell mortality during lethal stress. Because the REMFS configuration employed herein can be applied to whole body therapy, the present invention can be used for clinical interventions for various diseases and/or conditions, including but not limited to Alzheimer's disease and other degenerative conditions with aging. The present invention can be used for prophylactic treatment to reduce or prevent various diseases and/or conditions, as well as a treatment to reduce or prevent various diseases and/or conditions after such diseases and/or conditions have been diagnosed.

Low dose EMF was examined for its ability to stimulate non-thermal cell stress as a pathway for improved cellular longevity and protection. (Shallom, J. M., Di Carlo, A. L., Ko, D., Penafiel, L. M., Nakai, A., and Litovitz, T. A., 2002. Microwave exposure induces Hsp70 and confers protection against hypoxia in chick embryos. J Cell Biochem 86(3), 490-496.) More specifically, low dose EMF was examined as to whether non-thermal REMFS activates anti-aging and hormetic effects via the heat shock response. Some previous studies have indicated that extremely low frequency electromagnetic fields (ELF-EMF, 50 and 60 Hz) can enhance cultured cell functions (Han, L., Lin, H., Head, M., Jin, M., Blank, M., and Goodman, R., 1998. Application of magnetic field-induced heat shock protein 70 for presurgical cytoprotection. J Cell Biochem 71(4), 577-583; Pipkin, J. L., Hinson, W. G., Young, J. F., Rowland, K. L., Shaddock, J. G., Tolleson, W. H., Duffy, P. H., and Casciano, D. A., 1999. Induction of stress proteins by electromagnetic fields in cultured HL-60 cells. Bioelectromagnetics 20(6), 347-357; Tsurita, G., Ueno, S., Tsuno, N. H., Nagawa, H., and Muto, T., 1999. Effects of exposure to repetitive pulsed magnetic stimulation on cell proliferation and expression of heat shock protein 70 in normal and malignant cells. Biochem Biophys Res Commun 261(3), 689-694.).

Similar results were found with *Caenorhabditis elegans* (Junkersdorf, B., Bauer, H., and Gutzeit, H. O., 2000. Electromagnetic fields enhance the stress response at elevated temperatures in the nematode *Caenorhabditis elegans*. Bioelectromagnetics 21(2), 100-106.), *Drosophila melanogaster* (Michel, A., and Gutzeit, H. O., 1999. Electromagnetic fields in combination with elevated temperatures affect embryogenesis of *Drosophila*. Biochem Biophys Res Commun 265(1), 73-78.), and *Escherichia coli* (Chow, K., and Tung, W. L., 2000. Magnetic field exposure enhances DNA repair through the induction of DnaK/J synthesis. FEBS Lett 478(1-2), 133-136.). Chick embryo models show that 60-Hz magnetic field exposures, which are sufficient to directly induce heat shock proteins, can pre-condition against damage from subsequent stressors such as hypoxia.

As explained in more detail below, however, the use of REMFS in accordance with one or more embodiments of the invention does not directly activate the HSR. Advantageous aging effects may be achieved by utilizing a myriad of novel dosifications, wave lengths, and/or power levels in accordance with embodiments of the invention. These and other novel embodiments, which are more fully described below, are not taught, disclosed, or suggested by any known prior art. See, e.g., (DiCarlo, A. L., Farrell, J. M., and Litovitz, T. A., 1999. Myocardial protection conferred by electromagnetic fields. Circulation 99(6), 813-816) and ultraviolet light exposure (Dicarlo, A. L., Hargis, M. T., Penafiel, L. M., and Litovitz, T. A., 1999. Short-term magnetic field exposures (60 Hz) induce protection against ultraviolet radiation damage. Int J Radiat Biol 75(12), 1541-1549). EMF exposure can induce oxidative stress protection during heart cell hypoxia (Carmody, S., Wu, X. L., Lin, H., Blank, M., Skopicki, H., and Goodman, R., 2000. Cytoprotection by electromagnetic field-induced hsp70: a model for clinical application. J Cell Biochem 79(3), 453-459) as well as protect against lethal hyperthermia in *Sciara coprophila* eggs (Goodman, R., and Blank, M., 1998. Magnetic field stress induces expression of hsp70. Cell Stress Chaperones 3(2), 79-88), cardiac ischemia in rats (Albertini, A., Zucchini, P., Noera, G., Cadossi, R., Napoleone, C. P., and Pierangeli, A., 1999. Protective effect of low frequency low energy pulsing electromagnetic fields on acute experimental myocardial infarcts in rats. Bioelectromagnetics 20(6), 372-377), and cerebral ischemia in rabbits (Grant, G., Cadossi, R., and Steinberg, G., 1994. Protection against focal cerebral ischemia following exposure to a pulsed electromagnetic field. Bioelectromagnetics 15(3), 205-216).

To more clearly demonstrate select advantages of exemplary novel embodiments over the prior art, experimental designs were considered in view of the previous art regarding studies relating to ELF-EMF and EMF. Unlike the prior art systems and methods, REMFS, when applied in accordance with the teachings of one or more embodiments disclosed herein, may act on one or more novel mechanisms. While not being bound by any particular theories, Applicants have discovered that novel systems and methods using REMF may influence HSR and hormesis by at least two possible mechanisms. Firstly, REMF may disrupt the HSF1-Hsp90 complex, releasing Hsp90 and thereby pre-conditioning HSF1 for subsequent stresses. Secondly, REMF may enhance thermal-induced activation of HSF1. REMF appears to stimulate anti-aging or hormetic effects as evidenced by delays in phenotypic cellular changes associated with senescence as well as overall reduced cell death during severe stress. These data are discussed relative to possible clinical interventions especially as they relate to neuroprotection in Alzheimer's disease and other neurodegenerative conditions.

Exemplary Experimental Materials and Methods

The following protocols are provided to more clearly provide the reader of this disclosure with an understanding of exemplary novel systems and methods of the invention. Those skilled in the art with the benefit of this disclosure will understand that the disclosed protocols are merely exemplary methods for implementing one or more embodiments of the invention. Therefore, modifications, including the addition or omission of one or more steps, processes, and/or materials may be implemented without departing from the scope of claimed embodiments of the invention.

Cells, Reagents, Antibodies and Other Materials.

Human peripheral blood mononuclear cells (PBMN) and T cells were isolated from healthy donor venous blood (30-50 years old). Fibroblasts from HSF1 knockout mice (HSF1$^{-/-}$) were obtained as a kind gift from Dr. Douglas Feinstein (University of Illinois at Chicago) via Dr. Ivor Benjamin (University of Utah). PBMN were purified via Ficoll-Paque™ Plus gradient centrifugation (GE Healthcare Bio-Sciences AB/Amersham Biosciences, Uppsala, Sweden). RPMI 1640 medium, Phytohemagglutinin (PHA) and Interleukin-2 (IL-2) were purchased from Invitrogen (Carlsbad, Calif.). Both culture media contained penicillin/streptomycin (Sigma-Aldrich).

For Western blot and immunoprecipitation assays, polyclonal Hsp70 and Hsp90 antibodies as well as HSF1 monoclonal antibody were used in conjunction with horseradish peroxidase-linked anti-mouse secondary antibody purchased from StressGene (Ann Arbor, Mich.). Antibody to phosphotyrosine, 4G10, was purchased from Upstate Biotechnology, Inc. (Lake Placid, N.Y.). Hoechst 33342 was ordered from Sigma (St. Louis, Mo.). Protein silver staining kit was purchased from Owl (Portsmouth, N.H.). The DNA primer pair containing HSF1 consensus binding sequence (Heat shock element, HSE) was synthesized by Invitrogen (Carlsbad, Calif.). EMF system and chamber was supplied by the Department of Research Resources, University of Illinois at Chicago.

Cell Cultures.

Mouse fibroblasts were grown at 37.8° C., 5% $CO_2$, and 95% humidity in DMEM supplemented with 10% fetal calf serum, 400 mM glutamine and 100 U/ml penicillin/streptomycin. In the near-confluent state, cells were trypsinized and subcultured at a 1:2 ratio split while keeping record of the input and output cell number repeatedly until the end of their in vitro proliferative capacity. Cumulative population doubling level (CPDL) was monitored following the Hayflick system of replicative senescence (Rattan, S. I., and Sodagam, L., 2005. Gerontomodulatory and youth-preserving effects of zeatin on human skin fibroblasts undergoing aging in vitro. Rejuvenation Res 8(1), 46-57). In a series of experiments with mouse fibroblasts, CPDL 23 was designated as 100% of lifespan completed. These cultured cells were subjected to REMFS throughout their lifespan by putting the culture flasks in an EMF chamber and exposing cells at 50 MHz/0.5 W twice weekly for 0, 5, 15 and 30 minutes. Cultures were maintained at 37° C. for 30 min before the culture medium was changed.

T-Cell Isolation.

After informed consent, 50-60 mL of peripheral blood was obtained by venipuncture from human subjects ranging in ages of 30 to 50 years old. Peripheral blood mononuclear cells were isolated as previously described (Berger, 1979) and adjusted to 2×106/mL in AIM-V media (Gibco) supplemented with 0.25% Pentex Human Ex-Cyte (Bayer). Cells adherent to plasticware (monocyte-enriched fraction) were separated from lymphocyte-enriched nonadherent cells (lymphocytes). T-cells were isolated from lymphocyte enriched cell preparations by using BioMag SelectaPure™ human T-cell Enrichment systems (negative selection) as suggested by the manufacturer (Polysciences, Inc.).

Heat Shock Experiments.

T-cells were exposed to a transient heat shock by submerging parafilm wrapped plastic plates in a 41° C. circulating water bath for 30 minutes. Cells were harvested quickly and frozen in ethanol-dry ice baths for whole cell extracts (WCE) as previously described (Jurivich, D. A., Sistonen, L., Kroes, R. A., and Morimoto, R. I., 1992. Effect of sodium salicylate on the human heat shock response. Science 255(5049), 1243-1245).

Electromagnetic Field Exposures.

Electromagnetic Field Exposures were carried out using an IFI (Instruments For Industry Inc., N.Y. 11779) TEM Chamber (Transversal Electromagnetic Chamber, model CC110-SPEC, DC to 1,000 MHz, Test Equipment Corporation, Mountain View, Calif.) that was mounted vertically. The IFI TEM chamber contained a shelf which was used for sample placement.

Temperature Changes During EMF.

To verify that EMF did not induce heat shock-level temperatures, 37° C. cell culture media and distilled water were irradiated for 5, 15, and 30 minutes and monitored for temperature changes.

The Cumulative Population-Doubling Level (CPDL) Comparison in Mouse Fibroblasts with or without EMF Treatment.

Murine fibroblasts and human T cells were treated with EMF (50 MHz/0.5 W) twice weekly and the CPDL was determined by summing the population doublings between each subculture.

Co-Immunoprecipitation.

Lymphocytes were solubilized in 1% SDS containing 1% Protease Inhibitor Cocktail, then incubated at 4° C. overnight. After quickly defrosting to achieve cell fracture, non-specific IgG binding to protein was affected by addition of 1 mg of total lysate protein which was then incubated with 20 ml protein A/G sepharose at room temperature for 1 hour and centrifuged at 14,000 rpm for 5 min (4° C.). Thirty-microliters of anti-human HSF1 monoclonal antibody were added to the supernatant and incubated at room temperature for 2 hours, followed by 30 μl protein A/G sepharose incubated at 4° C. overnight. The immune complexes and sepharose beads were centrifuged at 14,000 rpm at room temperature for 5 min, the supernatant was aspirated and the beads were washed 10 times, 5 min each with 0.1% SDS in 1×PBS. Sixty-microliters loading buffer were added to the beads which were then boiled and loaded onto a 4-12% gradient Precast Gel. After electrophoresis, the gel was cut into two pieces where one piece was reserved for Coomassie blue or Silver stain and the other was utilized for transfer blotting to PVDF membrane.

Lactate Dehydrogenase (LDH) Measurement Assay.

T-lymphocyte death rate was assessed by measuring LDH released in culture media as an indicator of damage to the cell membrane using Promega's Cytotox 96q non-radioactive cytotoxicity assay kit (Madison, Wis., USA). Results were acquired by measuring the wavelength absorbance at 490 nm and normalizing to total LDH in the cells. Data were expressed as percent of maximum LDH released from a control sample of 100% dead cells.

Trypan Blue Viable Cell Count.

Cells were diluted 1-2×105 cells per mL in complete medium without serum. To 0.5 ml of the cell suspension, 0.1 ml of 0.4% Trypan Blue Stain was added and allowed to stand 5 minutes at room temperature. Viable cells excluding the stain were counted by hemocytometer microscopy.

Electrophoretic Mobility Shift Assay (EMSA).

The DNA probes for electrophoretic mobility shift assay (EMSA) were a 26-bp double-stranded oligonucleotide containing the HSF1 consensus binding sequence (5'-gcT AgA Agc TTc TAg AAg cTT cTA gc-3'). [$^{32}P$]ATP-labeled oligonucleotides were purified on a Sephadex G-50 M column (Pharmacia Biotech, Piscataway, N.J.). An aliquot of 5 μg of cellular protein was incubated with the labeled double-stranded probe (~50,000 cpm) in the presence of 5 μg of nonspecific blocker, poly(dI-dC), in binding buffer (10 mM Tris-HCl, pH 7.5, 100 mM NaCl, 1 mM EDTA, 0.2% Nonidet P-40, and 0.5 mM DTT) at 25° C. for 20 minutes. Specific competition of the HSF1 transcription factor for labeled probe was performed by adding unlabeled double-stranded oligonucleotide containing the heat shock element (100×), whereas nonspecific competition of HSF1-DNA binding was determined by addition of the unlabeled double-stranded oligonucleotide (100×, 5'-AGCTCAATCTCCCTGGGACTT-3') which does not bind HSF1. Monoclonal antibody to human HSF1 (2 μg) was incubated with whole cell extracts for 30 minutes at 4° C. before addition of the HSE-containing oligonucleotide probe to achieve "supershifting" of HSF1 bound to the HSE-containing probe. Each mixture was separated by electrophoresis on a 4% polyacrylamide gel in 1× Tris glycine EDTA buffer. Gels were vacuum dried and subjected to autoradiography and phosphoimage analysis.

Western Blotting.

Whole cell extracts were collected and separated by 10% SDS-PAGE under non-reducing conditions. The separated proteins were electroblotted onto polyvinylidene difluoride membrane and blocked for 1 hour at room temperature with Tris-buffered saline containing 1% BSA. The membranes were then exposed to a 1:1,000 dilution of the purified polyclonal IgG against either human Hsp70, Hsp90 or HSF1 at room temperature for 1 hour. After being washed, Hsp70, Hsp90 or HSF1 were detected on the membrane blots by HRP-conjugated secondary antibodies followed by electrochemiluminescence (ECL), (Amersham, Arlington Heights, Ill.). Tyrosine phosphorylation of HSF1 was identified by probing immobilon membranes with 4G10 monoclonal antibody and developing with ECL as described above. Equal protein was loaded in each lane and actin was used as a reference to normalize the Hsp70, Hsp90 and HSF1 protein levels relative to the actin level which does not change during stress.

Results of Exemplary Protocols.

REMFS Decreases T-Cell Mortality.

To determine if REMFS altered the usual pattern of cell death in cultured quiescent T cells and IL-2 stimulated lymphoblasts, these cells were monitored for cell death by LDH release and trypan blue exclusion over several days. Thus, T-lymphocyte mortality was assessed by two methods: LDH released into media and Trypan blue exclusion.

FIGS. 1A, 1B, 1C and 1D illustrate that REMFS decreases T-lymphocyte mortality. FIGS. 1A and 1B show results from proliferating, IL2 stimulated T cells. FIG. 1A is a bar graph representation of LDH values released into cell culture media as measured by absorbance spectroscopy. FIG. 1B is a line graph of T lymphoblast mortality every 3 to 4 days as measured by Trypan blue exclusion. FIGS. 1C and 1D show both LDH release and Trypan blue exclusion for quiescent T cells that were maintained in fresh media over a 7 day period. By the seventh day, a 30 minutes daily REMFS treatment reduced T cell death by 34%. Results are representative of 4 independent experiments. Bar graphs indicate the means of SE (n=4).

FIG. 1A shows different durations of REMFS affected LDH release into cell culture supernatant from IL-2 stimulated T-lymphocytes over a 3 week period. Initial experiments showed that two REMFS treatments reduced LDH release by 20% (p<0.05) during the first 4 days of culture. Cellular protection persisted 21 days during 5 additional REMFS treatments. The least variability between REMFS treatment times occurred with 30 minute REMFS exposure, thus this length of EMF exposure time was selected as the optimal treatment regime for T lymphoblasts.

FIG. 1B provides graphic analysis of reduced cell mortality after REMFS treatment as determined by Trypan blue exclusion. Similar to the LDH release assay, maximal Trypan blue exclusion was observed in cells treated with a 30 minute regimen of REMFS.

Quiescent T cells also show a significant protective effect from REMFS as defined by both the LDH-release and Trypan blue exclusion assays. FIG. 1C demonstrates a 34% reduction in LDH release compared to control cells after T cells were treated with 30 minutes of REMFS for 7 consecutive days (p<0.01). This result is further corroborated by Trypan blue exclusion. FIG. 1D shows how REMFS protects T cells from death over a 7 day period with a maximal benefit obtained from daily 30 minute treatments. These data demonstrate that both growing and quiescent T cells are protected by short and repetitive exposures to low dose REMFS.

REMFS Enhances HSF1-HSE Binding in T-Lymphocytes During Low Dose Thermal Stress.

Figure 2:
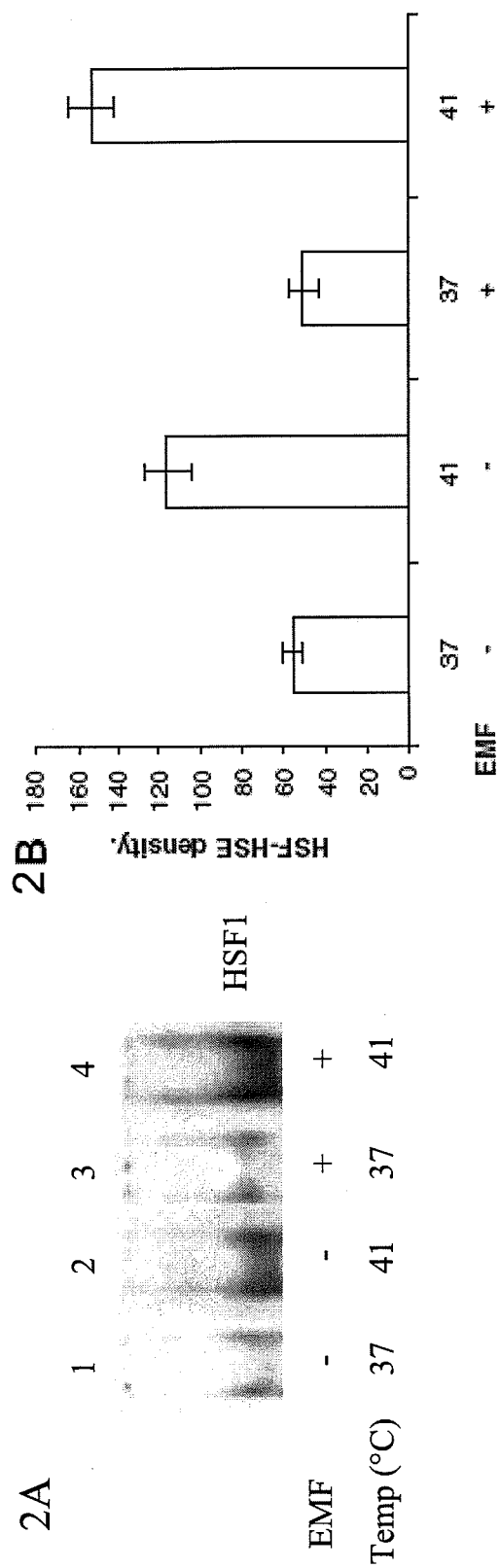
FIGS. 2A and 2B illustrate that EMF increases HSF1-HSE binding in T-lymphoblasts derived from human donor blood.

FIGS. 2A and 2B show results from an Electromobility Shift Assay for HSF1-HSE binding in IL-2 treated T lymphoblasts stimulated by a sub-lethal heat stress (41° C.) in accordance with one embodiment of the invention. More specifically, FIGS. 2A and 2B illustrate that EMF increases HSF1-HSE binding in T-lymphoblasts derived from human donor blood. FIG. 2A shows results from an electrophoretic mobility shift assay (EMSA) carried out with whole cell extracts of T-lymphoblasts with or without EMF treatment. EMF treatment preceded thermal stress and occurred every 3 days over a 21 day period. Protein-DNA complexes were separated by a 4% PAGE and subjected to autoradiography. The heat shock element (HSE) DNA probe consisted of the canonical sequence, 5'-gcT AgA Agc TTc Tag AAg cTT cTA g c-3'. EMSA lanes 1 and 3 show that 37° C. control cells (with or without REMFS) have minimal HSF1-HSE binding activity; however, lanes 2 and 4 show that a mild thermal stress for 30 minutes at 41° C. results in substantial HSF1-HSE binding activity, especially with the EMF-preconditioned T lymphoblasts.

FIG. 2B is a bar graph that displays phosphoimaging data that measures the relative values of the HSF1-HSE complexes. No difference in baseline, 37° C. HSF1-HSE binding is noted between EMF and non EMF treated cells, however, during a 41° C. heat shock, the EMF treated cells exhibit 33% greater HSF1-HSE binding than cells not treated with EMF. Results are representative of 3 experiments (means SE).

Molecular dynamic phosphoimaging reveals that the HSF1-HSE signal is 109.10 (arbitrary units of phosphor-signaling) for T cells exposed to 41° C. versus 145.14 arbitrary units for T cells preconditioned with REMFS and then heat stressed at 41° C. Thus, REMFS preconditioning of T cells resulted in a 33% increase in HSF1-HSE binding for a given stimulus.

REMFS Treatment Increases Inducible Levels of Hsp70 and Phosphorylated HSF1.

Figure 3:
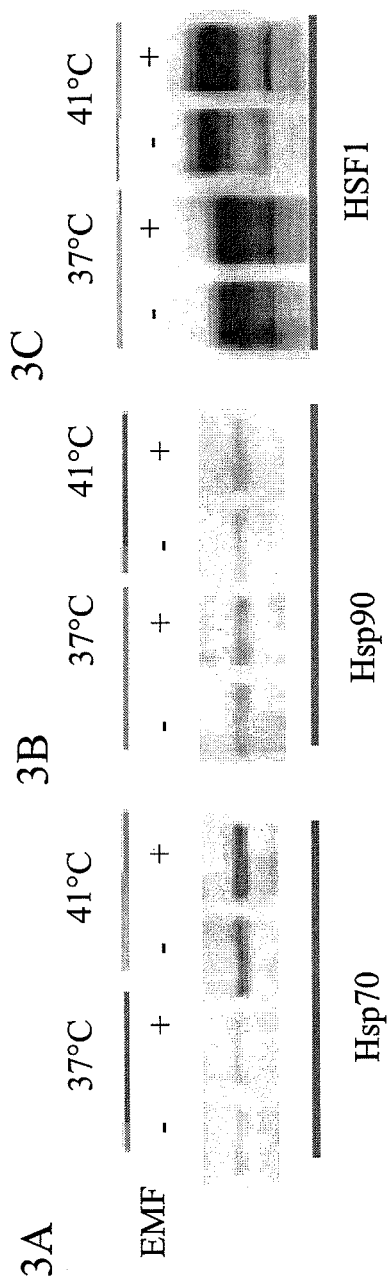
FIG. 3 illustrates Western blot analysis of Hsp70, Hsp90 and HSF1 in control and EMF-treated T lymphoblasts.

FIGS. 3A, 3B, and 3C illustrate Western blot analysis of Hsp70, Hsp90 and HSF1 in control and EMF-treated T lymphoblasts in accordance with one embodiment of the invention. Cells were treated with EMF for 30 minutes every two days for 14 days and then heat shocked for 30 minutes at 41° C. or maintained at 37° C. SDS-solubilized whole cell extracts were subjected to SDS-PAGE and western blot analysis. FIG. 3A demonstrates that Hsp70 increases after a 41° C. heat shock and that EMF preconditioning further enhances the Hsp70 signal. FIG. 3B shows that neither heat shock for 30 minutes or REMFS had any effect on Hsp90 protein levels. In FIG. 3C, HSF1 western blot analysis shows that REMFS has no effect on the amount or migration of HSF1 in SDS PAGE when cells are maintained at 37° C., however, upon 41° C. heat shock, HSF1 slows in its SDS PAGE migration and REMFS treatment is associated with higher levels of the slowly migrating HSF1, indicative of increased levels of HSF1 in its phosphorylated form. The results indicate that REMFS (50 Mhz/0.5 W) treatment increases HSF1 phosphorylation level and inducible level of Hsp70 but not Hsp90 in T lymphoblasts. Results are representative of 3 independent experiments.

REMFS therapy enhances HSF1 phosphorylation and Hsp70 expression as demonstrated in FIGS. 3A and 3C. FIGS. 3A and 3B show a representative western blot analysis of Hsp70 and Hsp90 protein levels in EMF treated and non-treated T lymphoblasts.

The most abundant heat shock protein, Hsp70, is found to increase after a mild 41° C. heat shock and the amount of inducible Hsp70 is even greater in heat shocked cells preconditioned with EMF over a 21 day period. By comparison, the less abundant Hsp90 did not change levels after heat shock in either the EMF treated or control cells. These results indicate that brief and mild heat shock treatment of T lymphoblasts preferential impacts Hsp70 and not Hsp90 levels.

Given that HSF1 phosphorylation is linked to maximal heat shock protein mRNA expression, Western Blot analysis for HSF1 was used to assess how extensively HSF1 migration is retarded in the SDS polyacrylamide gel as a general marker of HSF1 hyperphosphorylation. FIG. 3C shows a representative Western blot and HSF1 can be detected in control 37° C. cells as an approximately 70-kDa protein. REMFS treatment by itself neither increases the amount of HSF1 nor does it cause retardation of its migration in the gel. It was found that 41° C. treatment for 30 minutes causes HSF1 to become hyperphosphorylated and its migration in the gel is markedly retarded. By comparison, REMFS-treated lymphoblasts that were also heat shocked at 41° C. for 30 minutes display greater levels of HSF1 migrating to the area of hyper-phosphorylated HSF1 than non-treated, heat shocked lymphoblasts (i.e., a broader and more intense band).

These results demonstrate that REMFS boosts the heat shock response by enhancing the phosphorylation of HSF1 after heat shock compared to the non REMFS treated cells, thus resulting in higher levels of Hsp70.

REMFS Disrupts HSF1-Hsp90 Complex in T-Lymphocytes.

Figure 4:
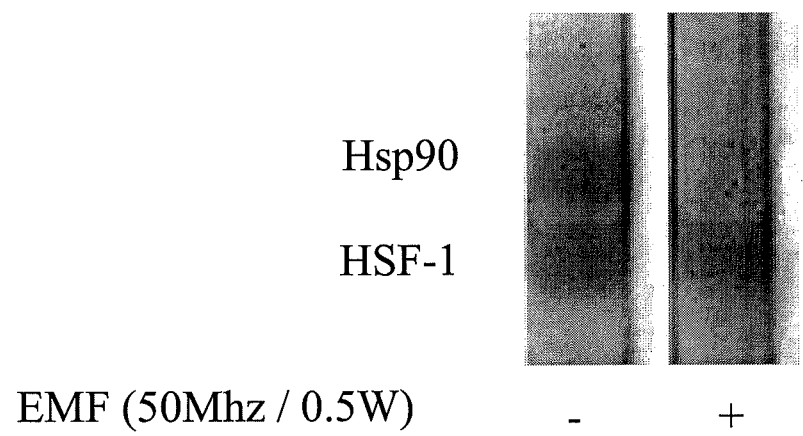
FIG. 4 illustrates silver stained SDS-PAGE of immunoprecipitated HSF1 and Hsp90 from whole cell T lymphocyte extracts, and shows that REMFS (50 MHz/0.5 W) treatment results in the disassociation of Hsp90 with HSF1.

Recognizing that Hsp90 is a strong modulator of the HSF1 activation and release of Hsp90 from the HSF1-Hsp90 complex activates the heat shock response (Harris, N., MacLean, M., Hatzianthis, K., Panaretou, B., and Piper, P. W., 2001. Increasing *Saccharomyces cerevisiae* stress resistance, through the overactivation of the heat shock response resulting from defects in the Hsp90 chaperone, does not extend replicative life span but can be associated with slower chronological ageing of nondividing cells. Mol Genet Genomics 265(2), 258-263), it was then examined whether REMFS altered the relationship of Hsp90 with HSF1 in T lymphocytes. As shown in FIG. 4, silver stained SDS-PAGE of immunoprecipitated HSF1 and Hsp90 from whole cell T lymphocyte extracts shows that REMFS (50 MHz/0.5 W) treatment results in the disassociation of Hsp90 with HSF1. Cells were maintained at 37° C. and EMF-treated cells were exposed to 30 minutes of EMF every other day for 14 days. Results are representative of 3 independent experiments.

FIG. 4 shows unbound Hsp90 and HSF1-Hsp90 complexes in T-Lymphocytes. By co-immunoprecipitation of HSF1 and Hsp90 it is evident that REMFS treated T lymphocytes have little to no Hsp90 associated with HSF1 when compared to non-treated cells.

REMFS Rescues Old Fibroblasts from Senescent Changes In Vitro.

Figure 5:
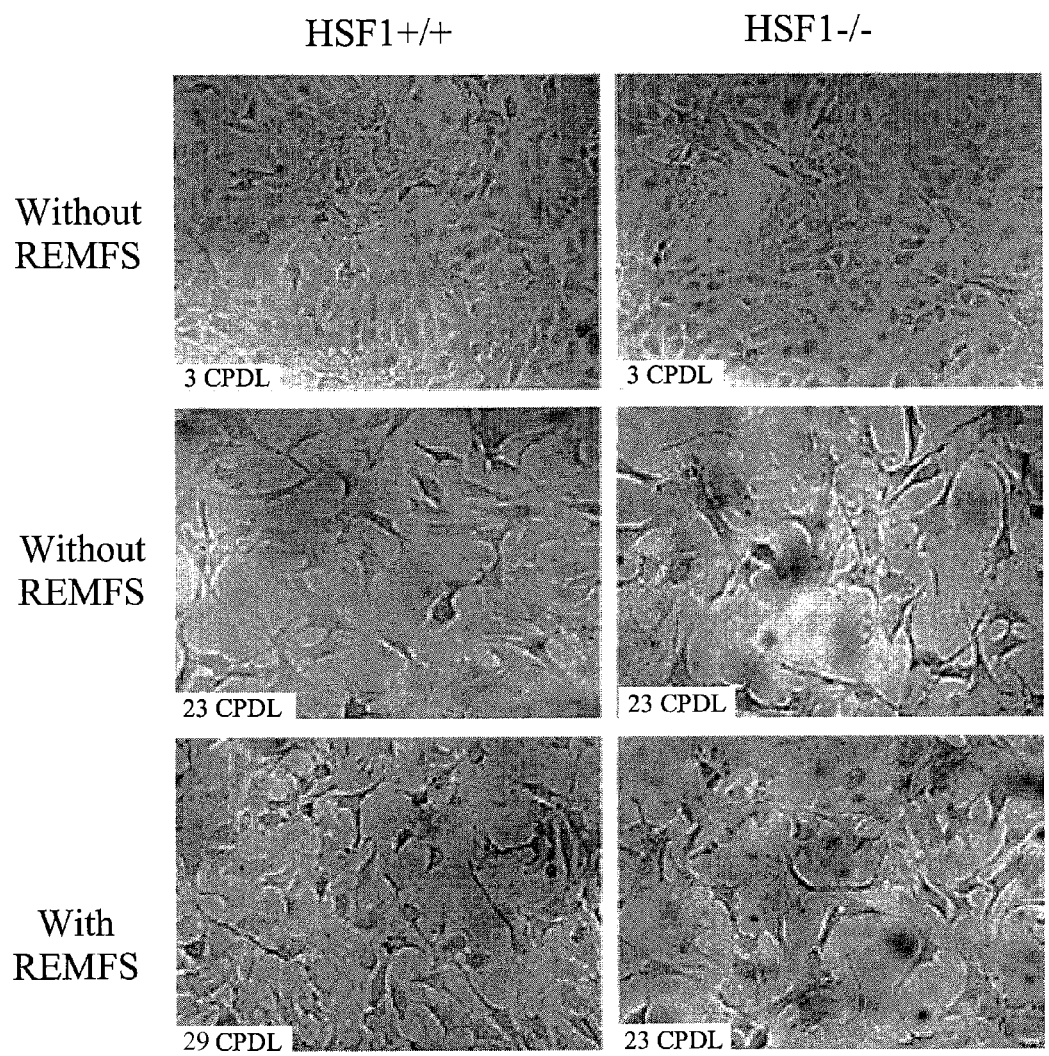
FIG. 5 illustrates REMFS changes the senescence morphology of wild type mouse fibroblasts (HSF1$^{+/+}$), but does not change HSF1 knockout fibroblasts (HSF1$^{-/-}$).

Because some of the REMFS effects appear to interface with HSF1, experiments were designed to compare HSF1 knockout fibroblasts with wild type cells. Furthermore, a question that can be raised is whether REMFS altered age dependent changes in serially passaged fibroblasts. To this end, wild type and HSF1$^{-/-}$ mouse fibroblasts at 23 cell population doubling (CPDL), which represents 100% of lifespan completed, were treated with REMFS twice weekly for two weeks. FIG. 5 shows photographs of these cells in culture. As shown in FIG. 5, REMFS changes the senescence morphology of wild type mouse fibroblasts (HSF1$^{+/+}$) but not HSF1 knockout fibroblasts (HSF1$^{-/-}$). After treating fibroblasts with REMFS twice weekly for two weeks, wild type fibroblasts appeared to recover their proliferative capacity and revert to a more youthful phenotype. Results represent 3 independent experiments.

It was found that when cells traverse from CPDL 3 to 23, they become a senescent phenotype which displays larger, vacuolated cells with more diverse morphotypes than cells at earlier cumulative population doublings (CPDL). It was found that REMFS treatment (50 MHz/0.5 W) partially reversed and delayed age-related enlargement and diversification of cell morphology in the HSF1$^{+/+}$ but not HSF1$^{-/-}$ murine fibroblasts. The observed REMFS effects included cells that remained small sized and more spindle-shaped in addition to fewer multinucleated cells and a more parallel positioning of the cells. REMFS also extended the replicative lifespan (29 CPDL) of mouse fibroblast HSF+/+ in a cell population which already appeared to reach its terminal lifespan (23 CPDL).

REMFS Increases Proliferative Lifespan.

Figure 6:
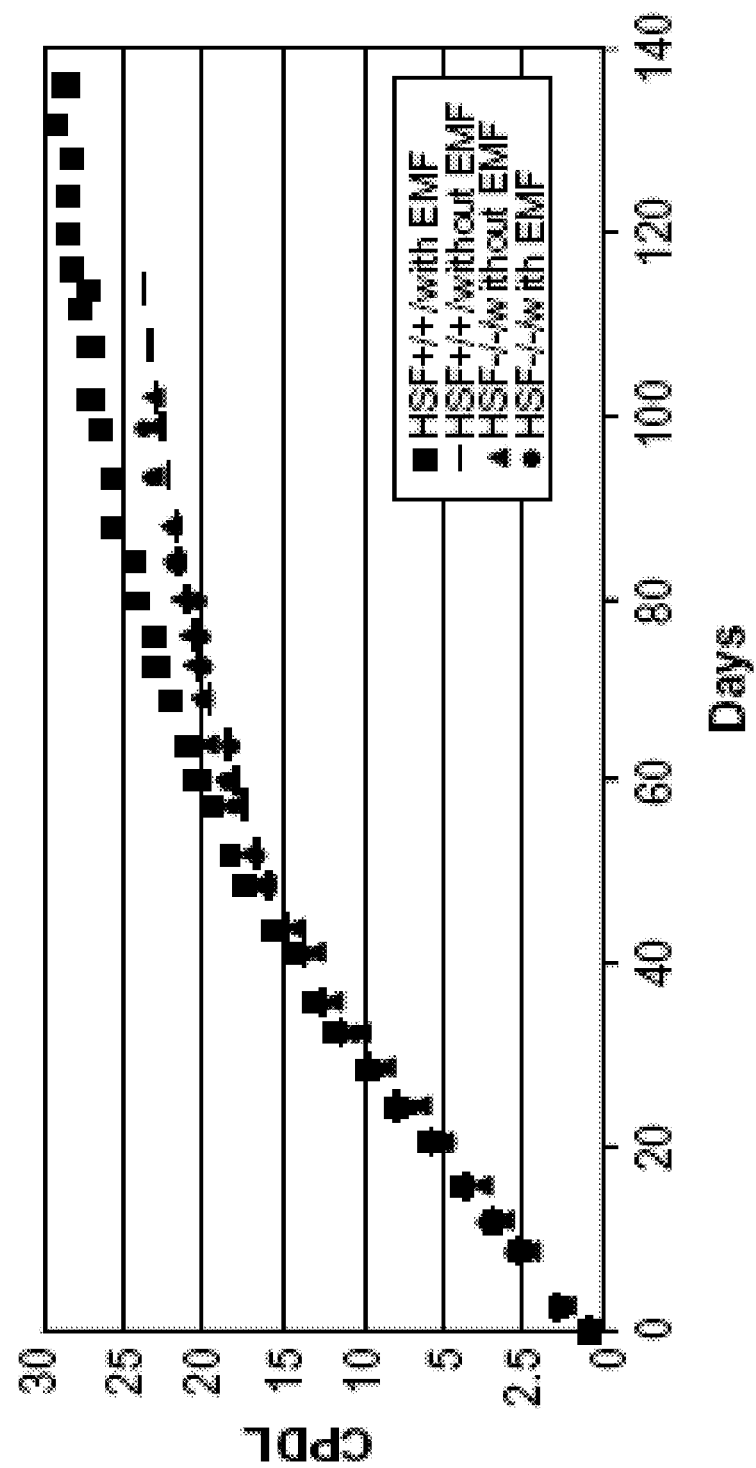
FIG. 6 illustrates longevity and proliferative curves in two cell lines of mouse fibroblasts (HSF1$^{+/+}$ and HSF1$^{-/-}$) with and without REMFS.

Cumulative population-doubling level (CPDL) curves of 2 primary cell lines of mouse fibroblast are shown in FIG. 6. More specifically, FIG. 6 illustrates longevity and proliferative curves in two cell lines of mouse fibroblasts (HSF1$^{+/+}$ and HSF1$^{-/-}$) with and without REMFS. The results show increased lifespan and proliferative life in the HSF$^{+/+}$ cell line treated with REMFS, whereas no differences in proliferation life span is seen with REMFS-treated HSF1-knockout cells.

Both HSF1 +/+ and HSF −/− fibroblasts grew at similar rates until cumulative population-doubling level (CPDL) 18. REFMS appears to retard the decline in cell proliferations rates, especially after CPDL 18. REMFS treated wild type fibroblasts had a proliferative lifespan of about 138 days compared to 118 days observed with the non-treated wild type fibroblasts. This difference represents a 17% increase in lifespan potential. Fibroblasts with HSF1-knockouts did not demonstrate a hormetic response to REMFS and only achieved maximum CPDL of 23 with a total replicative life span of 100 days.

The results presented here provide novel evidence that REMFS treatment stimulates beneficial hormetic effects on cultured lymphocytes as well as fibroblasts. Both non-replicative and replicative cells demonstrate positive biological responses to REMFS, suggesting an important hormetic effect. By analyzing different components of the heat shock response, the evidence points towards REMFS-induced hormesis being mediated, in part, by strengthened molecular responses to stress.

Initial observations revealed that REMFS protects human peripheral blood T lymphocytes from progressive cell death that occurs during in vitro culture conditions. Based on low LDH released into cell culture media and reduced Trypan blue dye uptake, both quiescent and IL-2 stimulated T cells survive longer after REMFS stimulation than non-treated cells. The effects were most pronounced in quiescent T cells, thus suggesting that post-mitotic cells such as neurons may maximally benefit from REMFS therapy. Anti-death effects by REMFS were found to be most pronounced in the first few days of T cell IL-2 stimulation. Because the vast majority of these cells were not yet dividing, this observation is consistent with REMFS most avidly impacting quiescent cells or those that are in the G0 or G1/S boundary of the cell cycle. Based on REMFS experiments with quiescent T cells, it appears that at least 4 REMFS treatments (one treatment daily for 30 minutes) are optimal for hormetic effects. Those of skill in the art will recognize that in accordance with the present disclosure, upper limits of REMFS efficacy can be readily determined for implementations in accordance with one or more embodiments of the invention. It is noted, however, that studies on pharmacological manipulation of cell protective responses report U-shaped dose-responses where low and high doses of a particular drug are ineffective and a narrow range of drug concentration is optimal for strengthening cell protection (Jurivich, D. A., Sistonen, L., Kroes, R. A., and Morimoto, R. I., 1992. Effect of sodium salicylate on the human heat shock response. Science 255(5049), 1243-1245). A larger dose-response profile for the most optimal impact of REMFS on cell defense systems can be determined by those of skill in the art in accordance with the present disclosure.

Because REMFS protected T cells, one question that can be raised is how REMFS affects cellular stress responses, particularly the heat shock response. While monitoring HSF1 activation in accordance with embodiments of the invention, REMFS may not induce a classical heat shock response at 37° C. as evidenced by lack of HSF1-HSE binding activity that is normally induced after a 40 to 42° C. heat shock for several minutes. REMFS does not alter cell culture temperature, thus, it is believed that biological effects from REMFS are unlikely due to cellular responses to thermal injury. Of course, the heat shock response can occur at 37° C. with toxic stimuli such as heavy metals, however, these types of stimuli typically occur at the boundary of cell death, and REMFS did not cause cell death. Rather than directly induce a full fledged heat shock response, REMFS appears to partially influence HSF1, which is the primary transcription factor for enhancing the production of heat shock protein mRNA during cellular stress.

In accordance with certain novel systems and methods of the invention, REMFS may influence HSF1 in two ways. Firstly, novel uses of REMFS may be applied to disrupt the molecular brake of HSF1-DNA binding, namely, Hsp90. REMFS-treated cells have less Hsp90-HSF1 complexes than non treated cells, and it is known that disruption or depletion of Hsp90 can facilitate the heat shock response (Harris, N., MacLean, M., Hatzianthis, K., Panaretou, B., and Piper, P. W., 2001. Increasing Saccharomyces cerevisiae stress resistance, through the overactivation of the heat shock response resulting from defects in the Hsp90 chaperone, does not extend replicative life span but can be associated with slower chronological ageing of nondividing cells. Mol Genet Genomics 265(2), 258-263). One mechanism thought to disassociate Hsp90 from HSF1 is the accumulation of damaged proteins (Buchner, J., 1999. Hsp90 & Co.—a holding for folding. Trends Biochem Sci 24(4), 136-141). Typically, during heat shock, Hsp90 levels decline as damaged proteins accumulate. By contrast, REMFS at 37° C. did not alter Hsp90 levels as seen in heat shock. Without being tied to a particular theory, one possible explanation for the lack of declining Hsp90 levels is that REMFS, as applied in accordance with embodiments of the invention, cause protein unfolding rather than irreversible damage and aggregation. This process would still promote Hsp90 binding and repair of the unfolded proteins but in this instance no Hsp90 degradation would take place as it moves to the proteosome. On the other hand, there is no a priori reason to believe that REMFS unfolds protein and therefore a novel mechanism of REMFS-induced dissociation of Hsp90 and HSF1 can be considered. Unlike heat shock, REMFS does not lead to decreased intracellular levels of Hsp90. Thus, full activation of the heat shock response may require both dissociation of Hsp90 from HSF1 and its overall degradation. Secondly, application of REMFS in accordance with certain embodiments appears to strengthen HSF1 phosphorylation during thermal stress. In unstressed lymphocytes treated with REMFS, there was no increase of HSF1 phosphorylation, but when REMFS treated cells were exposed to a mild heat shock, HSF1 phosphorylation was enhanced compared to heat shock alone. Taken together, these observations suggest that, at least in certain applications, REMFS pre-conditions cells to stress and puts them closer to inducing the full heat shock response for a given toxic stimulus. Furthermore, REMFS causes HSF1 to be modified in a way that ultimately leads to higher levels of Hsp70 during stress. It is believed that cell protection is proportional to the levels of Hsp70. The most likely mechanism for this effect is the enhanced mRNA production generated by improved heat shock gene expression mediated by hyper-phosphorylated HSF1. Alternatively, REMFS may induce a larger pool of HSF1 unassociated with Hsp90, thus strengthening transcription of the heat shock 70 protein gene by shifting the equilibrium towards HSF1 trimers unencumbered by Hsp90. Other, although less likely possibilities are believed to be that REMFS stabilizes Hsp70 half-life or improves translation of the heat shock message RNA. The fact that Hsp90 does not increase in levels after REMFS treatment negates a translational mechanism of REMFS impact on the heat shock response.

Why REMFS preferentially leads to the accumulation of Hsp70 and not Hsp90 during the early part of heat shock is not clear. However, these results are consistent with previous studies on repeated mild heat shock (RMHS) treatment which reduces Hsp90 levels (Zhao, C., Hashiguchi, A., Kondoh, K., Du, W., Hata, J., and Yamada, T., 2002. Exogenous expression of heat shock protein 90 kDa retards the cell cycle and impairs the heat shock response. Exp Cell Res 275(2), 200-214). Additionally, a lag occurs between Hsp70 and Hsp90 production in cells, perhaps due to the fact that Hsp90 is a putative negative regulator of HSF1-DNA binding. It is believed that a mechanism to delay Hsp90 production relative to other heat shock proteins can be a means to maximize HSF1 function early in the heat shock response. This process eventually would create a feedback loop that allows cells to down-regulate the heat shock response. The possibility exists that REMFS selectively influences different components of the heat shock response, namely, the activation rather than the de-activation process.

In addition to REMFS impact on the heat shock response, it appears that REMFS can influence in vitro senescence. Surprisingly, REMFS reversed age-related morphology to a youthful appearance and it maintained functional and proliferative (CPDL) characteristics usually lost during proliferative senescence. REMFS did not transform senescent fibroblasts into cancer-like cells as these cells eventually acquired the senescent phenotype. It is believed that longevity enhancement of fibroblasts is linked to HSF1 because fibroblasts lacking this transcription factor did not respond to REMFS-induced cellular life extension. The above findings confirm a link between HSF1 to aging and longevity. A reduction in HSF1 activity accelerates tissue aging and shortens life-span whereas its over-expression or mutation extends lifespan in nematodes (Hsu, A. L., Murphy, C. T., and Kenyon, C., 2003. Regulation of aging and age-related disease by DAF-16 and heat-shock factor. Science 300(5622), 1142-1145).

Because repetitive mild heat shock (RMHS) studies report reversal of morphological age-related changes in human fibroblasts similar to findings with REMFS, consideration can be given as to how the two treatments possibly overlap in their mechanism of action. It appears that the application of REMFS in accordance with embodiments of the invention has a different mechanism of action than RMHS as set forth in the prior art. For example, the application of REMFS in accordance with certain embodiments does not directly activate the heat shock response with regard to elevating heat shock proteins during non-stressful conditions. Rather, it seems to precondition and enhance the cellular stress response when cells are provoked by toxic stimuli. Given HSF1's central role in the process of detoxifying aggregated protein that occurs during senescence (Cohen, E., Bieschke, J., Perciavalle, R. M. Kelly, J. W., and Dillin, A., 2006. Opposing activities protect against age-onset proteotoxicity Science 313:1604-1610), the data presented here suggest that measures to push HSF1 towards its activated state are essential to cellular longevity, at least where proliferative lifespan is concerned. REMFS may extend the proliferative potential of a small population which retain some proliferative potential within a larger population of non-proliferating senescent cells or reverse the senescent phenotype.

As shown in the present disclosure, REMFS can favorably influence the first part of the human heat shock response. The present disclosure can be incorporated into various new therapies. For example, unlike thermal conditioning of stress responses that can not reach deep tissue, REMFS can be applied to any organ of interest without inducing thermal damage and thus "precondition" the organ to different types of cellular stress. Therefore, REMFS therapy holds potential promise against death-inducing stimuli such as hypoxia, toxic amyloid aggregation or cytotoxic neurotransmitters. Given that the discovery that HSF1 is the critical factor in prevention of age-onset proteotoxicity (Cohen, E., Bieschke, J., Perciavalle, R. M. Kelly, J. W., and Dillin, A., 2006. Opposing activities protect against age-onset proteotoxicity Science 313:1604-1610), the embodiments of the present invention provide therapies having beneficial effects of REMFS on HSF1 function, and the therapies of the present disclosure can be used to reduce or eliminate protein-associated diseases.

In the examples disclosed herein, an IFI TEM Chamber (model CC 110 SPEC, DC to 1,000 MHz, Test Equipment Corporation, Mountain View, Calif.) was used. This therapeutic device can be controlled using a device having a computer-readable medium comprising computer-executable instructions that when executed by a processor may be provide application of REMFS subjects, such as humans. Details of an exemplary exposure systems are shown in FIG. 7 and FIG. 8 and further described below.

Exemplary TEM Systems.

Figure 7A:
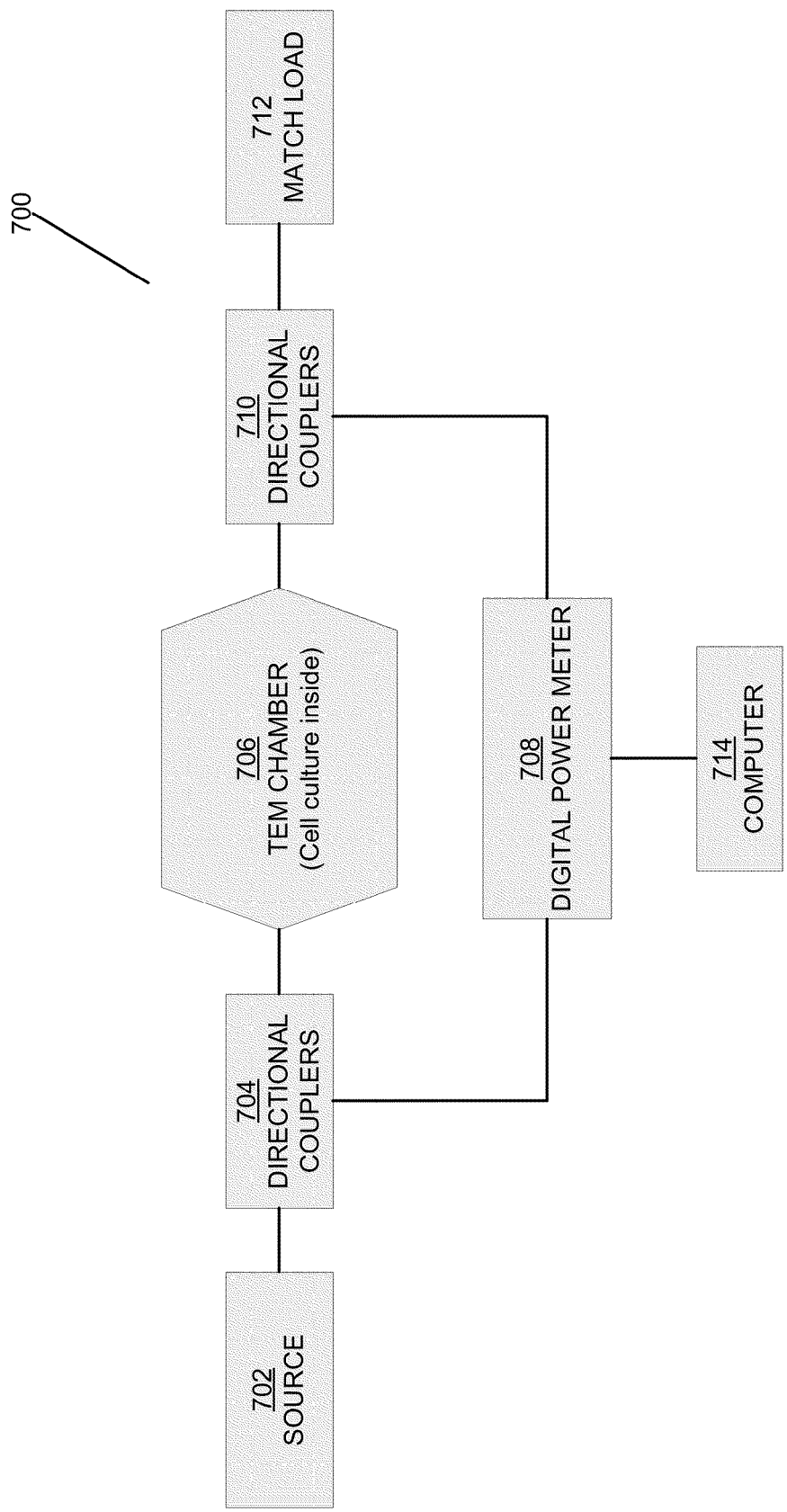
FIG. 7a shows an exemplary exposure system that may be configured to irradiate cells for cellular senescence and FIG. 7b shows an exemplary system that may be configured for the treatment of one or more organs of a patient's body.
Figure 7B:
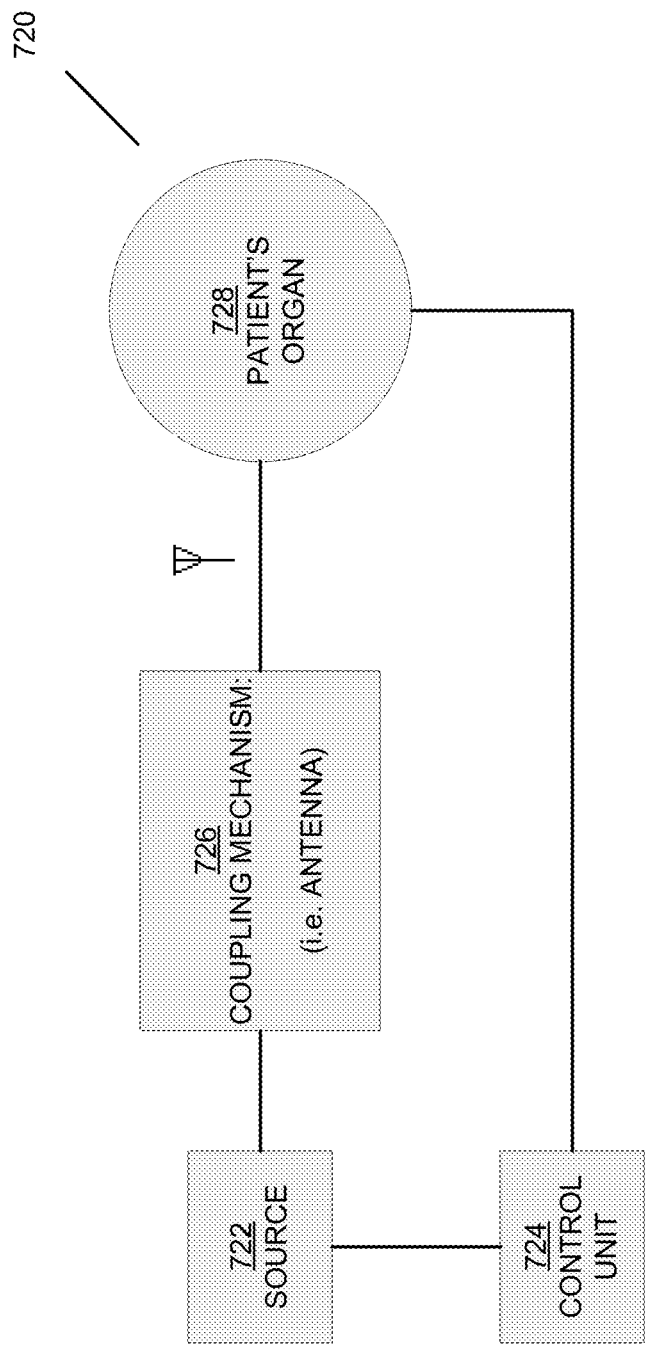
Figure 8:
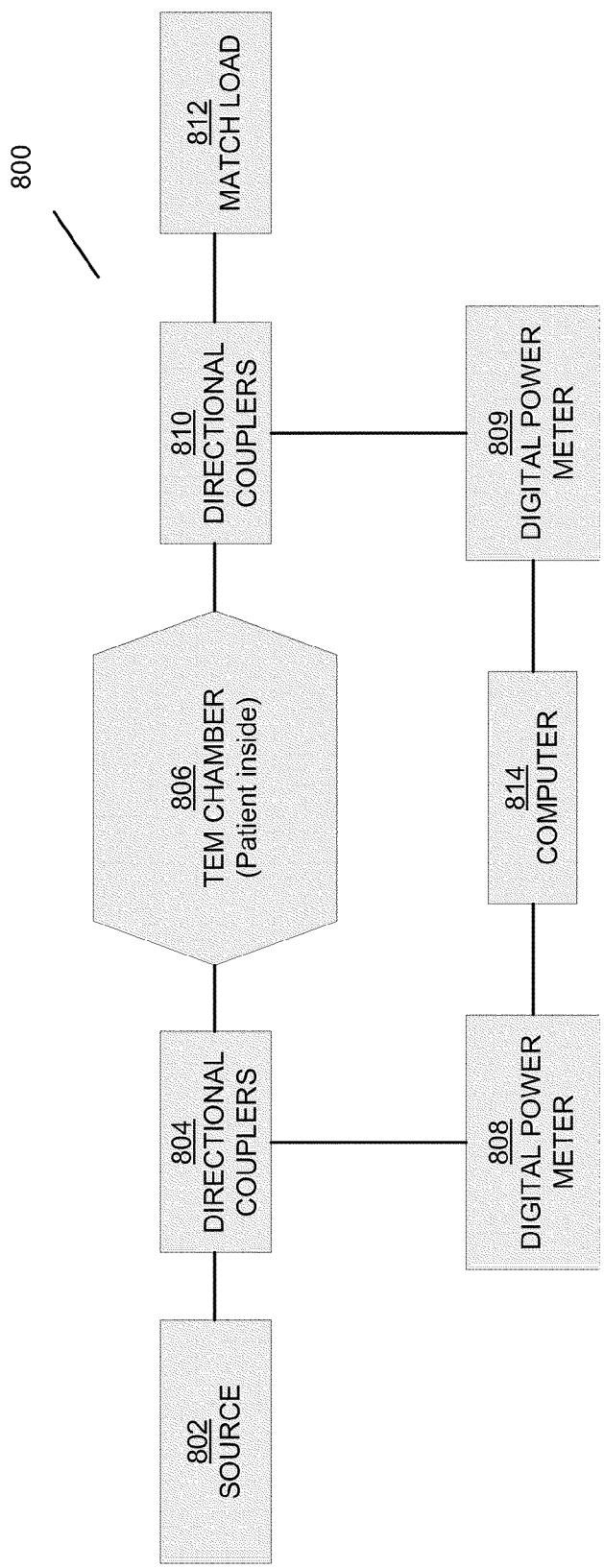
FIG. 8 illustrates an apparatus adapted to deliver REMFS to the entire body of a patient in accordance with an embodiment of the invention.

FIGS. 7a and 7b show exposure systems or apparatuses according to exemplary embodiments of the invention. Specifically, FIG. 7a shows an exemplary exposure system 700 that may be configured to irradiate cells for cellular senescence and FIG. 7b shows an exemplary system 720 that may be configured for the treatment of one or more organs of a patient's body. Looking first to FIG. 7a, the system 700 may comprise a source 702, which may be a wave generator. In one embodiment, a function generator is used in conjunction with an amplifier. As shown in FIG. 7a, the source 702 is connected to a first coupler(s) 704. First coupler(s) 704 can be connected to TEM chamber 706, and power meter 708. In addition to being connected to first coupler(s) 704, power meter 708 can be connected to a second coupler(s) 710, which is also connected to TEM chamber 706. As seen in FIG. 7a, second coupler(s) 710 can also be connected to match load 712.

The system or apparatus 700 can be operatively connected to an electronic computing device, such as computer 714. The computer 714 comprises a computer-readable medium having computer-executable instructions that when executed by a processor may control application of REMFS from the system 700. In one embodiment, the computer-readable instructions, when executed, perform a method for delivering REMFS to cells. As used herein, a computer-readable medium may include one or more physical mediums located at one or more physical locations. In one embodiment, at least two remote physical mediums are connected through a network, such as an intranet, or the Internet. Those skilled in the art will also readily appreciate in view of this disclosure that the selection of a processor for executing the computer-readable instructions on the computer-readable medium may depend on a myriad of factor, including but not limited to, costs, desired speed, the amount of power required for specific implementations, and combinations thereof.

In one embodiment, the TEM chamber 706 is tapered at each end to a transition section that includes type N coaxial jacks for signal connection. In one embodiment, the IFI TEM Cell model CC110 (DC to 1000 MHz) was utilized. The exposure chamber 706 may be configured to operate as a 50Ω (ohms) impedance matched system. This system simulates free-space exposure when is terminated in its characteristic impedance of 50Ω (match load). The wave impedance throughout the TEM chamber 706 may be very close to the intrinsic impedance of free space of 377Ω (ohms). In accordance with embodiments of the invention, the TEM chamber's dimensions should not exceed one third of the volume between the septum and the walls of the TEM cell to ensure that the test object "sees" a uniform field.

Specifically referring to embodiments in which the TEM chamber 706 comprises the IFI TEM CELL model CC110, the TEM chamber 706 will comprise a rectangular metallic section containing a flat-metal-strip center conductor located between the top and bottom of the chamber 706, which is used for sample placement. The field or power density in the plane midway between the center conducting strip and the cell wall is fairly uniform and the introduction of a sample, for example, a cell culture, into the chamber 706 alters the field distribution slightly. In accordance with embodiments of the invention, mice, insects, worms, isolated preparations (cells, stem cells, and tissues) can be placed in the center of chamber 706 or at several preselected locations to assure equal exposure to each specimen.

In accordance with certain embodiments, an incident power of 0.5 W was used. A "power management system" may comprise the directional couplers 704, 710 to get the incident and reflected waves and digital power meter(s) 708 with a built-in GPIB (General Purpose Interface Bus) to properly interface with the computer 714 on the input and output ports of the TEM chamber 706. In one embodiment, computer-executable instructions on a computer-readable medium may measure and average the incident and reflected powers and calculate a mean value for the absorbed power (herein after "$P_{absorbed}$"). In one embodiment, the input, output, and reflected powers may be monitored and used to determine the absorbed power using the differential-power technique (for example in an enclosed exposure system). In accordance with one exemplary embodiment, the power absorbed by the empty exposure device is: $P_{empty}$=(net incident power)−(net transmitted power). When the sample is placed in the exposure device, we have $P_{with\ sample}$=(net incident power)−(net transmitted power) Then, the power absorbed by the sample is determined by Pabsorbed= $P_{with\ sample} - P_{empty}$.

Thus, in accordance with one embodiment, to determine the SAR (Specific Absorption Rate) [watts/kg], $P_{absorbed}$ may be divided by the mass of the sample. Thus, where the sample is a cell culture, the incident electric field ($E_{inc}$) may be: $E_{inc}$=(PR)1/2/d, where P=$P_{absorbed}$, R=50 ohms, d=septum height (distance between the center conductor and the top chamber wall).

As shown in FIG. 7b, an exemplary system may be configured to deliver localized REMFS to a portion of a patent's body, such as a targeted organ. As used herein, the term "patient" may include any living animal, including humans. As shown, system 720 comprises a source 722. Source 722 may be similar in structure and/or operation to source 702, shown in FIG. 7a. The system 722 further comprises a control unit 724, which may comprise a digital power meter 708 and a computer 714 (as shown in FIG. 7a).

The system 720 further includes a coupling mechanism 726, such as an antenna. In accordance with certain embodiments of the invention, there are different kinds of antennas 726 that can be used for localized and partial-body exposure, for example, to expose a patient's organ 728 (i.e. the brain cells of a patient). Such antennas may include, but are not limited to: loop antennas, interstitial antennas, implanted and/or embedded antennas, microstrip applicators or patch antennas, waveguides antennas, antenna arrays, and combinations thereof.

In one embodiment, the method comprises receiving an input indicative of an orientation of at least a localized region of a patient's body. In one embodiment, the input may be entered by a technician. The input is not required to explicitly define the orientation, but rather may be derived from information relation to the portion of the body and its orientation. For example, a technician wanting to target the brain of the patient may provide an input that is different than when targeting the heart of a patient. Yet in other embodiments, at least one parameter of the input may be sensed (electrically, mechanically, or electromechanically) by one or more devices. In such embodiments, at least one parameter may be automatically provided.

The computer readable medium within a computer, such as computer 714 and/or control unit 724 may contain instructions for initiating a first transmission of an amount of radio frequency electromagnetic energy (RFEM). The RFEM energy may be transmitted for at least about 5 minutes from an electromagnetic field source through the at least one directional coupler. The transmission of the RFEM is based upon the received input and is configured to improve either HSF1 or HSR function, or HSF1 and HSR function, without initiating a classical heat shock response. A second transmission of the amount of RFEM energy may be transmitted at a second transmission to the same region of the patient's body that received the first transmission of RFEM energy. In one embodiment, the first and the second transmission of the RFEM energy is configured to disrupt the molecular brake of HSF1-DNA binding without resulting in a decline of Hsp90. The computer-executable instructions may be configured to instruct any device to transmit the RFEM energy at about 50 MHz/0.5 W continuous radiation.

FIG. 8 shows an exemplary system 800 that may be configured to deliver REMFS to the entire body of a patient. Like system 700 shown in FIG. 7a, the system 800 may comprise a source 802, directional couplers 804, 810, TEM chamber 806, digital power meter(s) 808, 809, match load 812, and a computer 814. In one embodiment, the outside dimensions of the exposure chamber 806 are length: 13 m, width: 6.1 m, and height: 7.3 m (See D. A. Hill, "Human Whole-Body Radiofrequency Absorption Studies Using a TEM-Cell Exposure System", IEEE Trans, Microwave Theory Tech. vol. 30, No. 11, pp. 1847-1854, 1982). In one embodiment, subjects may be placed on a center conductor table (not shown) that may be positioned at the center of the chamber 806 in different body orientations with respect to the TEM wave.

In one embodiment, the energy absorbed by humans in the chamber 806 can be determined as in the exposure system shown and described in relation to FIG. 7a by using precision directional couplers 804, 810 and power meters 808, 809 monitoring the input, output, and reflected powers and then determine the absorbed power using the differential-power technique. Digital power meters 808, 809 may interface with the computer 814 where a computer-readable medium may have computer-executable instructions that when executed, measure the incident, reflected powers, and calculates the value for the absorbed power.

TEM chambers, such as TEM chamber 806, can also be used for human exposure at frequencies below or equal to 50 MHz and therefore provide wavelengths that are typically on the order 10 m in length and 6 m in height and width (Allen, S J. Measurements of power absorption by human phantoms immersed in radio-frequency fields. Ann NY Acad. Sci. 1975; 247: 494-8; Hill, D A. Human whole-body radiofrequency absorption studies using a TEM-cell exposure system. IEEE Trans. Microwave Theory Tech. 1982; 1847). The radio frequency electromagnetic (RFEM) energy absorbed by humans in a TEM chamber can be determined by using precision directional couplers and power meters.

When using the TEM chamber for human exposure, subjects are placed in the center of a chamber in different body orientations with respect to the TEM wave. This assures uniform exposure to the region of interest. Total exposure is recommended to be no greater than 1 Watt according to a number of international and national organizations including the American National Standards Institute (ANSI) and the IEEE (IEEE Committee on Man and Radiation (1995), Technical Information Statement on: Human Exposure to Microwaves and Other Radio Frequency Electromagnetic Fields. IEEE Engineering in Medicine and Biology Magazine. 1995; 14: 336-337. As described in relation to FIG. 7b, it is also possible to specifically irradiate organs with antennas depending on the type of disease (brain, heart, etc). A review of the currently available literature on RFEM energy provides evidence that biological effects occur at a specific absorption rate (SAR) of about 1 Watt/kg. Evidence indicates that this SAR can be tolerated by human beings. SARs of about 4 W/kg represent the threshold of potentially harmful effects. Prolonged exposure to whole-body-averaged SARs of 0.4 W/kg or less does not appear to be harmful. In consideration of engineered negligible senescence, the REMFS therapy disclosed herein applies SARs below this recommendation; therefore, it appears to that the methodology of the present invention can apply to human therapy.

Further embodiments relate to a product or kit having an apparatus for transmitting REMFS and instructions for using the apparatus in one or more treatments to a patient that includes the transmission of the REMFS. The term "instructions" is not limited to print-based materials. Nor are the instructions required to be physically distributed with the apparatus. Rather, the instructions may be provided online. For example, in one embodiment, the manufacturer or distributer of the apparatus may have a collection of one or more instructions for operating the apparatus that are in electronic format. In one such embodiment, the instructions are available on an intranet or the Internet on one or more computer-readable mediums.

In one embodiment, the product or kit includes an apparatus having a power source operatively connected to at least one directional coupler. The apparatus may be configurable to transmit repetitive electromagnetic field shock at about 50 MHz/0.5 W continuous radiation. The product or kit may further comprise instructions for operating said apparatus, that if executed, indicate an orientation of at least a portion of a patient's body in relation to the at least one directional coupler during the transmission of the continuous radiation. The instructions are provided such that, if followed, either HSF1 or HSR function, or HSF1 and HSR function of target cells within said portion of the patient's body is improved without initiating a classical heat shock response in those target cells.

In one embodiment, the instructions provide at least two treatment protocols, wherein at least one protocol provides an indication for transmitting the continuous radiation for a first time duration and a second time duration, wherein the first and the second time duration are at least about 1 day apart. Exemplary protocols may indicate a repetition of the continuous radiation for about once a day, about once every two days, about once every three days, wherein the repetitive electromagnetic field shock comprises about 30 minutes per day, about once a week, and about twice a week In further embodiments, the instructions may indicate one or more benefits of the specific treatment protocols. In one embodiments, the instructions provide an indication that the transmission of the continuous radiation from the apparatus will either (1) disrupt the molecular brake of HSF1-DNA binding without resulting in a decline of Hsp90, (2) extend the replicative lifespan of the at least one living cell within the portion of the patient's body, (3) delay the average age-related enlargement and diversification of at least one living cell, (4) reverts at least one living cell to a more youthful phenotype within the portion of the patient's body, or (5) any combination of (1) through (4).

It is thus apparent that the present disclosure teaches systems and methods comprising the use of repetitive electromagnetic field shock to at least one living cell, wherein the repetitive electromagnetic field shock improves HSF1 and/or HSR function. The repetitive electromagnetic field shock can comprise about 30 minutes per day every two days of about 50 MHz/0.5 W continuous radiation. The repetitive electromagnetic field shock can comprise about 30 minutes per day every three days of about 50 MHz/0.5 W continuous radiation. The repetitive electromagnetic field shock can comprise about 30 minutes per day about twice a week of about 50 MHz/0.5 W continuous radiation. The repetitive electromagnetic field shock can be applied to the at least one cell until the cell reaches cellular senescence. The at least one cell can be a T cell.

In one embodiment, repetitive electromagnetic field shock is delivered to a plurality of living cells, which can include but are not limited to brain cells. In a further embodiment, the repetitive electromagnetic field shock is delivered to a plurality of in vivo living cells, which can include but are not limited to brain cells.

In one embodiment, the repetitive electromagnetic field shock is delivered to a localized region of the body of a patient.

In another embodiment, the repetitive electromagnetic field shock is delivered to the entire body of a patient.

In one embodiment, the repetitive electromagnetic field shock is provided by a transversal electromagnetic cell. The transversal electromagnetic cell can be vertically mounted on a base.

In accordance with one embodiment, an apparatus is provided that comprises an electromagnetic field source and a computer programmed to control the delivery of repetitive electromagnetic field shock from the electromagnetic field source to at least one living cell, wherein the repetitive electromagnetic field shock improves HSF1 function. The apparatus can deliver repetitive electromagnetic field shock that comprises about 30 minutes of about 50 MHz/0.5 W continuous radiation. The apparatus can provide repetitive electromagnetic field shock to the at least one cell until the cell reaches cellular senescence. The electromagnetic field source can comprise a transversal electromagnetic cell. The transversal electromagnetic cell can be vertically mounted on a base. The apparatus can comprise at least one electromagnetic field shock emitting surface area to deliver repetitive electromagnetic field shock to a localized region of the body of a patient. The at least one electromagnetic field shock emitting surface area can be adapted to deliver repetitive electromagnetic field shock to brain cells of a patient. The emitting surface area can comprise at least one antenna. The at least one electromagnetic field shock emitting surface area can be adapted to deliver repetitive electromagnetic field shock to the entire body of patient.

Biological Model

Both genetic and environmental interventions can retard age-related processes, albeit at various rates (Butler, R N, Miller, R A, Perry, D, Carnes, B A, Williams, T F, Cassel, C, Brody, J, Bernard, M A, Partridge, L, Kirkwood, T, Martin, G M and Olshansky, S J. New model of health promotion and disease prevention for the 21st century. Brit Med J. 2008; 337: 149-150; Valenzano, D R, Terzibasi, E, Genade, T, Cattaneo, A, Domenici, L and Cellerino, A. Resveratrol prolongs lifespan and retards the onset of age-related markers in a short-lived vertebrate. Curr Biol. 2006; 16: 296-300). Accumulated evidence points to two main pathways that regulate aging: the heat shock response mediated through Heat shock factor 1 (HSR/HSF1) and the alternative stress pathway controlled by DAF-16/FOXO (Garigan, D, Hsu, A L, Fraser, A G, Kamath, R S, Ahringer, J and Kenyon, C. Genetic analysis of tissue aging in *Caenorhabditis elegans*: a role for heat-shock factor and bacterial proliferation. Genetics. 2002; 161: 1101-12). The HSR/HSF1 pathway primarily induces chaperones. These highly conserved proteins across multiple species participate in repair and maintenance functions, protein folding and disaggregation, polymer transport across biological membranes, and ubiquitinated molecule degradation. Ultimately, chaperones prevent accumulation of abnormal proteins which in turn can promote longevity. Optimal HSR is essential for cell survival; whereas, inefficient and altered HSR results in abnormal growth and development as well as accelerated aging and apoptosis (Rattan, S I and Derventzi, A. Altered cellular responsiveness during ageing. Bioessays. 1991; 13: 601-6; Soti, C and Csermely, P. Molecular chaperones and the aging process. Biogerontology. 2000; 1: 225-33).

In the absence of stress, HSF1 rests in an un-activated state constrained by self-folding and Hsp90 juxtaposed as a molecular brake. Hsp90 prevents HSF1-DNA binding (Satyal, S H, Chen, D, Fox, S G, Kramer, J M and Morimoto, R I. Negative regulation of the heat shock transcriptional response by HSBP1. Genes Dev. 1998; 12: 1962-74; Zou, J, Guo, Y, Guettouche, T, Smith, D F and Voellmy, R. Repression of heat shock transcription factor HSF1 activation by HSP90 (HSP90 complex) that forms a stress-sensitive complex with HSF1. Cell. 1998; 94: 471-80). Different forms of stress cause HSF1 to unfold, become hyper-phosphorylated, and form homo-trimers that acquire DNA binding capability. One possible cause of disrupted HSF1-Hsp90 complexes during stress is the accumulation of denatured polypeptides that attract Hsp90 from HSF1 (see FIG. 9). (See also Zou, J, Guo, Y, Guettouche, T, Smith, D F and Voellmy, R. Repression of heat shock transcription factor HSF1 activation by HSP90 (HSP90 complex) that forms a stress-sensitive complex with HSF1. Cell. 1998; 94: 471-80; Bharadwaj, S, Ali, A and Ovsenek, N. Multiple components of the HSP90 chaperone complex function in regulation of heat shock factor 1 In vivo. Mol Cell Biol. 1999; 19: 8033-41; Guo, Y, Guettouche, T, Fenna, M, Boellmann, F, Pratt, W B, Toft, D O, Smith, D F and Voellmy, R. Evidence for a mechanism of repression of heat shock factor 1 transcriptional activity by a multichaperone complex. J Biol Chem. 2001; 276: 45791-9).

Figure 9A:
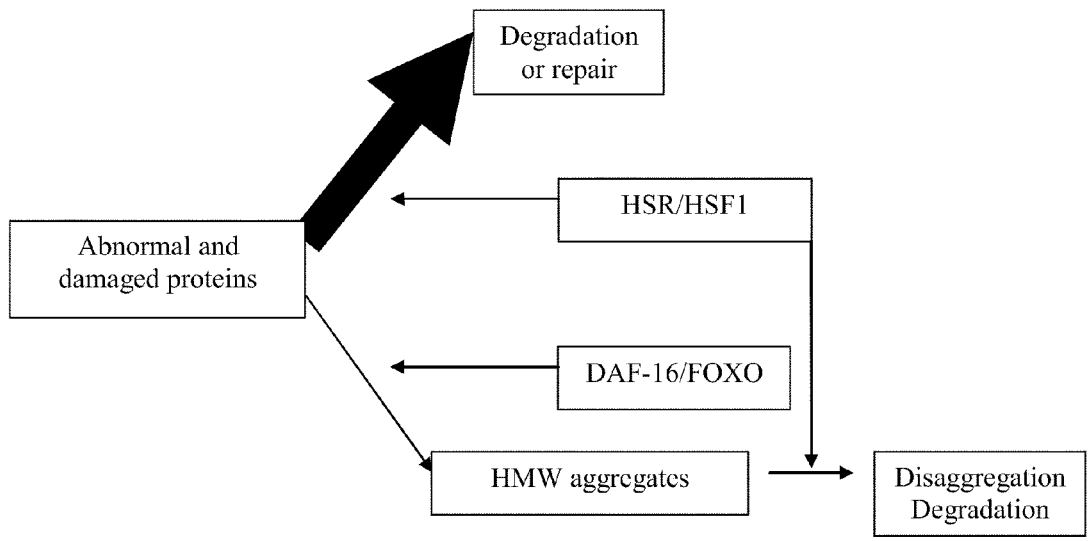
FIGS. 9a and 9b show block diagrams illustrating the effect of aging on longevity pathways.
Figure 9B:
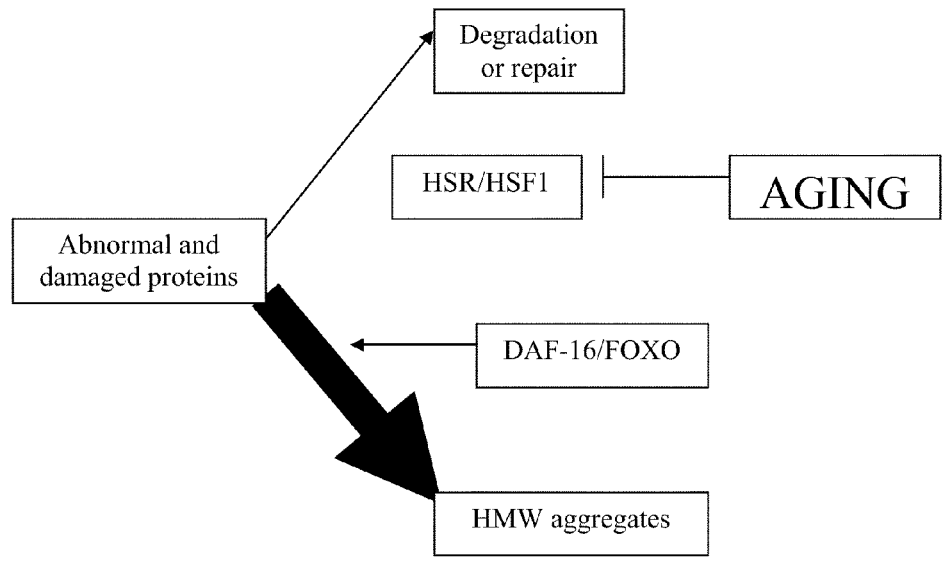

FIG. 9 illustrates the effect of aging on longevity pathways. As shown in FIG. 9, Pathway A, a preferred pathway, is HSR/HSF1; abnormal proteins are degraded and there is no protein aggregate production. Pathway B shows how aging negatively regulates HSR/HSF1; alternatively, the DAF-16/FOXO is activated and produces high-molecular weight aggregates that accumulate due to malfunction of the repair and degradation system.

During stress recovery, HSF1 trimers re-associate with Hsp90 complexes (Satyal, S H, Chen, D, Fox, S G, Kramer, J M and Morimoto, R I. Negative regulation of the heat shock transcriptional response by HSBP1. Genes Dev. 1998; 12: 1962-74; Zou, J, Guo, Y, Guettouche, T, Smith, D F and Voellmy, R. Repression of heat shock transcription factor HSF1 activation by HSP90 (HSP90 complex) that forms a stress-sensitive complex with HSF1. Cell. 1998; 94: 471-80). In addition to chaperone-HSF1 interactions, HSF1 function is likely regulated by its phosphorylation status. Thus, protein-protein interactions, phoshorylation and self assembly are at least 3 potential regulatory points that are essential to HSF1 regulation and aging. Additional considerations are rRNA interactions with HSF1, overall HSF1 protein levels and other as yet undefined inhibitors (Shamovsky, I and Gershon, D. Novel regulatory factors of HSF-1 activation: facts and perspectives regarding their involvement in the age-associated attenuation of the heat shock response. Mech Ageing Dev. 2004; 125: 767-75; Qiu, L, Welk, J F and Jurivich, D A. Ultraviolet light attenuates heat-inducible gene expression. J Cell Physiol. 1997; 172: 314-22).

Reduced HSF1 activity accelerates tissue aging and shortens life-span (Garigan, D, Hsu, A L, Fraser, A G, Kamath, R S, Ahringer, J and Kenyon, C. Genetic analysis of tissue aging in Caenorhabditis elegans: a role for heat-shock factor and bacterial proliferation. Genetics. 2002; 161: 1101-12). In addition, HSF-1 overexpression extends lifespan by approximately 40% and gives increased resistance to heat and oxidative stress on Drosophila melanogaster and Caenorhabditis elegans (Tatar, M, Khazaeli, A A and Curtsinger, J W. Chaperoning extended life. Nature. 1997; 390: 30; Kurapati, R, Passananti, H B, Rose, M R and Tower, J. Increased hsp22 RNA levels in Drosophila lines genetically selected for increased longevity. J Gerontol A Biol Sci Med Sci. 2000; 55: B552-9; Yokoyama, K, Fukumoto, K, Murakami, T, Harada, S, Hosono, R, Wadhwa, R, Mitsui, Y and Ohkuma, S. Extended longevity of Caenorhabditis elegans by knocking in extra copies of hsp70F, a homolog of mot-2 (mortalin)/mthsp70/Grp75. FEBS Lett. 2002; 516: 53-7).

Figure 10:
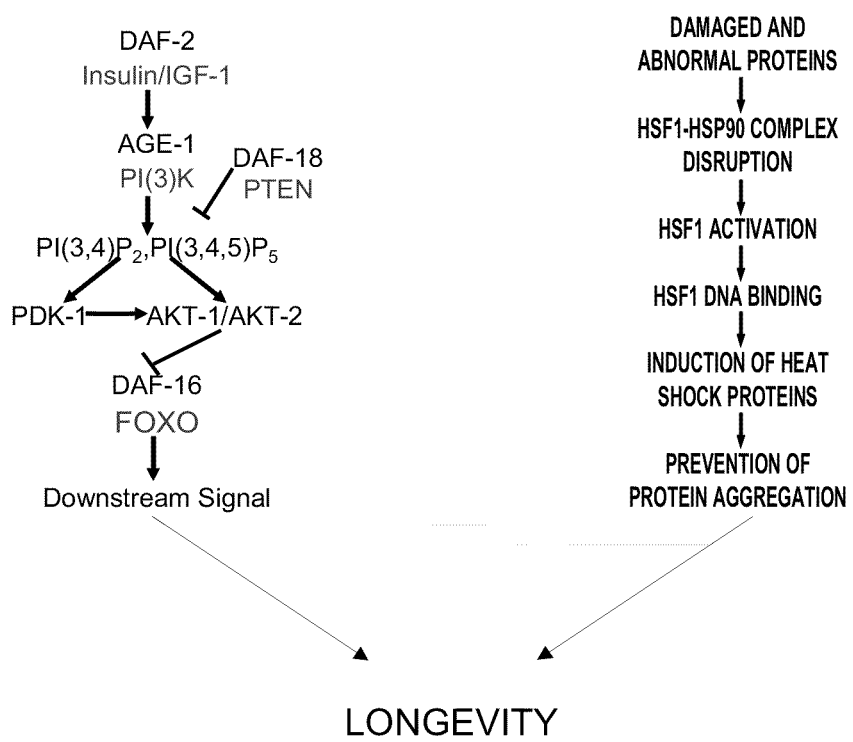
FIG. 10 illustrates that DAF-16 (FOXO) and HSR/HSF1 are two main pathways that control longevity.

Comparable to stress signaling, insulin/insulin-like growth factor-1 (IGF-1) signaling appears to regulate aging. This pathway negatively regulates the forkhead box class of proteins (FOXO), such as transcription factor DAF-16. Several studies indicate that DAF-16 promotes longevity (see FIG. 10, which illustrates that DAF-16 (FOXO) and HSR/HDF1 are the main pathways that control longevity). Caloric restriction and Resveratrol activate the silent mating type information regulation 2 homolog (SIRT1). The SIRT1 deacetylates FOXO transcriptional factors that contribute to cellular regulation (reaction to stressors, longevity). REMFS therapy enhances the HSR/HSF1 pathway. HSR/HSF1 controls protein repair and deregulation and prevent protein aggregation, also contributing to longevity.

Studies that indicate that DAF-16 promotes longevity include Kenyon, C, Chang, J, Gensch, E, Rudner, A and Tabtiang, R. A C. elegans mutant that lives twice as long as wild type. Nature. 1993; 366: 461-4; Henderson, S T and Johnson, T E. daf-16 integrates developmental and environmental inputs to mediate aging in the nematode Caenorhabditis elegans. Curr Biol. 2001; 11: 1975-80; Lee, R Y, Hench, J and Ruvkun, G. Regulation of C. elegans DAF-16 and its human ortholog FKHRL1 by the daf-2 insulin-like signaling pathway. Curr Biol. 2001; 11: 1950-7. This factor functions along the insulin/IGF-1 signaling pathway (Gems, D and Partridge, L. Insulin/IGF signaling and ageing: seeing the bigger picture. Curr Opin Genet Dev. 2001; 11: 287-92; Guarente, L and Kenyon, C. Genetic pathways that regulate ageing in model organisms. Nature. 2000; 408: 255-62). In C. elegans, DAF-16 is controlled by the activity of the DAF-2 insulin receptor, repressing DAF-16 activity through phosphorylation and cytoplasmic retention (Lin, K, Hsin, H, Libina, N and Kenyon, C. Regulation of the Caenorhabditis elegans longevity protein DAF-16 by insulin/IGF-1 and germline signaling. Nat Genet. 2001; 28: 139-45). In the absence of DAF-2/insulin receptor signaling or through its inhibition, DAF-16/FOXO moves into the nucleus and regulates transcription of its targets. One of the longevity interventions, dietary restriction (DR), activates this pathway. The sirtuin family members SIRT1 and SIRT2 are upregulated in response to DR, leading to deacetylation and enhanced transcriptional activation of DAF-16/FOXO, offering a potential mechanism coupling DR and this pathway in mammals (Wang, F, Nguyen, M, Qin, F X F and Tong, Q. SIRT2 deacetylates FOXO3a in response to oxidative stress and caloric restriction. Aging Cell. 2007; 6: 505-514). Despite the linkage of DAF-16 with longevity, recent experiments raise concerns about its direct role in slowing the aging process (Saul, N, Pietsch, K, Menzel, R and Steinberg, C E. Quercetin-mediated longevity in Caenorhabditis elegans: Is DAF-16 involved? Mech Ageing Dev. 2008; 10:611-13). Nevertheless, various stimulants of DAF-16 such as repeated thermal stress and exposure to plant polyphenols appear to improve lifespan and perhaps offer anti-aging effects (Kampkotter, A, Timpel, C, Zurawski, R F, Ruhl, S, Chovolou, Y, Proksch, P and Watjen, W. Increase of stress resistance and lifespan of Caenorhabditis elegans by quercetin. Comp Biochem Physiol B Biochem Mol Biol. 2008; 149: 314-23).

Similar to genetic manipulation of HSF1, changes in DAF-16 expression shortens life-span, and promoting DAF-16 activity increases life-span (Hsu, A L, Murphy, C T and Kenyon, C. Regulation of aging and age-related disease by DAF-16 and heat-shock factor. Science. 2003; 300: 1142-5). DAF-2-insulin/IGF-1 receptor mutations extend life-span, but only in the presence of DAF-16 and HSF1. Overall, a pecking order for longevity is apparent whereby HSR/HSF1 is the preferred pathway and DAF-16/FOXO is the backup pathway used mainly under severe stress conditions and during aging (Cohen, E, Bieschke, J, Perciavalle, R M, Kelly, J W and Dillin, A. Opposing activities protect against age-onset proteotoxicity. Science. 2006; 313: 1604-10).

During usual senescence, the HSR/HSF1 pathway declines. This decline is undoubtedly due to a variety of factors, but its failure is mostly attributable to a decrease in HSF1-DNA binding (Udelsman, R, Blake, M J, Stagg, C A and Holbrook, N J. Endocrine control of stress-induced heat shock protein 70 expression in vivo. Surgery. 1994; 115: 611-6; Perez, F P, Ilie, J I, Zhou, X, Feinstein, D and Jurivich, D A. Pathomolecular effects of homocysteine on the aging process: a new theory of aging. Med Hypotheses. 2007; 69: 149-60).

Figure 11A:
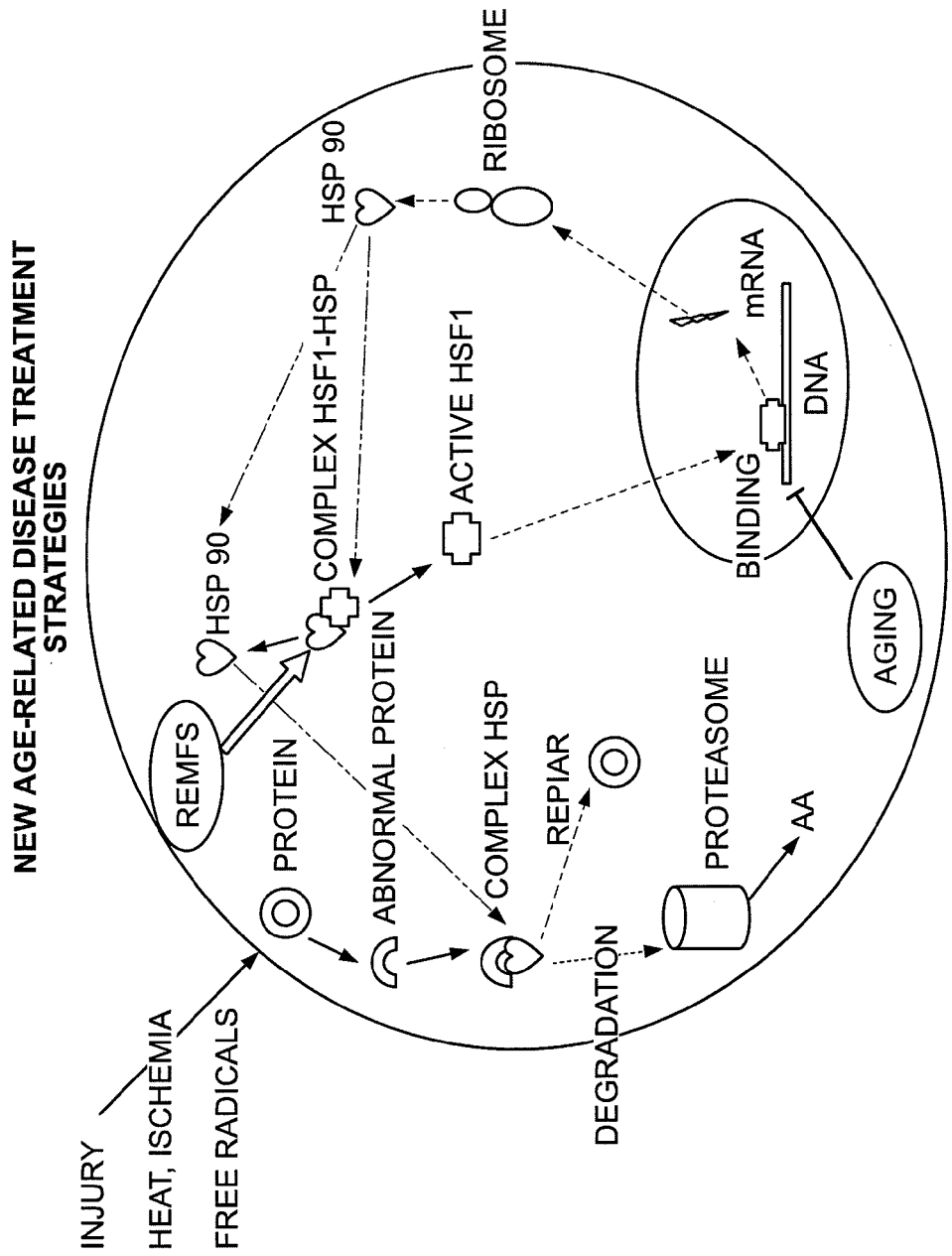
FIGS. 11a and 11b illustrates HSR and HSF1 activation by REMFS therapy.
Figure 11B:
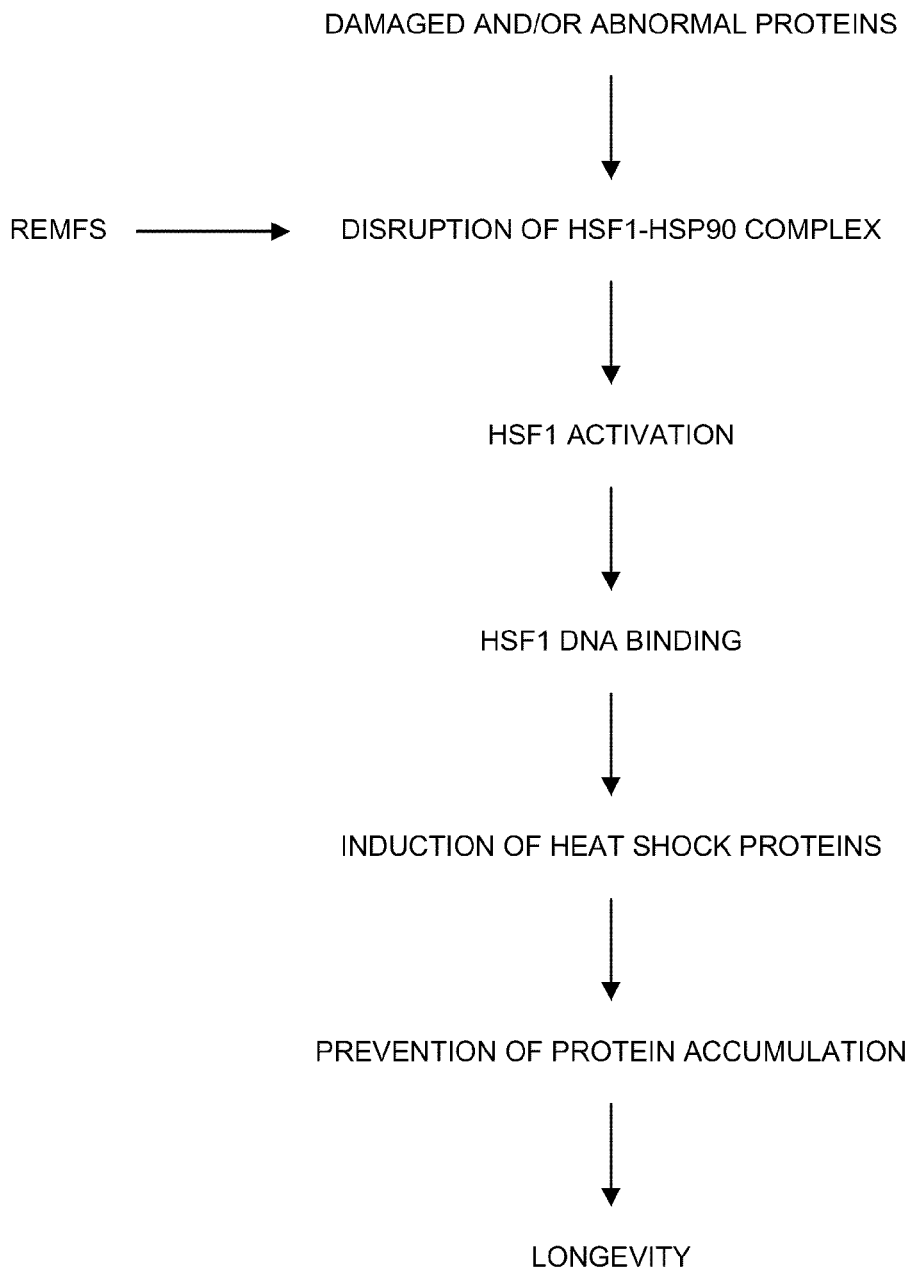

FIG. 11 illustrates HSR and HSF1 activation by REMFS therapy in accordance with one embodiment of the invention. In one embodiment, REMFS therapy counteracts the attenuation of the HSR/HSF1 pathway during aging. REMFS causes disruption of the HSF1 complex and preconditions the HSR for subsequent stresses.

Oxidation and homocysteine-mediated cross-linking of this long lived transcription factor may reduce its DNA binding activity; however, age-acquired inhibitors of HSF1 are suggested (Shamovsky, I and Gershon, D. Novel regulatory factors of HSF-1 activation: facts and perspectives regarding their involvement in the age-associated attenuation of the heat shock response. Mech Ageing Dev. 2004; 125: 767-75). In addition, chaperone inducibility and some chaperone functions decrease during aging (Soti, C and Csermely, P. Aging and molecular chaperones. Exp Gerontol. 2003; 38: 1037-40). These effects result in proteotoxicity and cellular degeneration (Arslan, M A, Csermely, P and Soti, C. Protein homeostasis and molecular chaperones in aging. Biogerontology. 2006; 7: 383-389; Morley, J F, Brignull, H R, Weyers, J J and Morimoto, R I. The threshold for polyglutamine-expansion protein aggregation and cellular toxicity is dynamic and influenced by aging in *Caenorhabditis elegans*. Proc Natl Acad Sci USA. 2002; 99: 10417-22; Nardai, G, Csermely, P and Soti, C. Chaperone function and chaperone overload in the aged. A preliminary analysis. Exp Gerontol. 2002; 37: 1257-62).

Perhaps to compensate for loss of the HSR/HSF1 pathway, the DAF-16/FOXO pathway activates during aging (Pardo, P S, Lopez, M A and Boriek, A M. FOXO transcription factors are mechanosensitive and their regulation is altered with aging in the respiratory pump. Am J Physiol Cell Physiol. 2008; 294: C1056-66). Although recent evidence suggests that basal DNA binding activities of FOXO are similar among different age groups, the down-regulatory effect on FOXO during is different between young and old mice. The age-dependent difference is attributed to signal transduction defects associated with stress protein kinase, JNK (c-Jun NH2-terminal kinase) in aged tissues (Pardo, P S, Lopez, M A and Boriek, A M. FOXO transcription factors are mechanosensitive and their regulation is altered with aging in the respiratory pump. Am J Physiol Cell Physiol. 2008; 294: C1056-66). JNK phosphorylates 14-3-3 directly, thus releasing its FOXO substrate and causing FOXO nuclear translocation which in turn activates genes to increase stress resistance (Oh, S W, Mukhopadhyay, A, Svrzikapa, N, Jiang, F, Davis, R J and Tissenbaum, H A. JNK regulates lifespan in *Caenorhabditis elegans* by modulating nuclear translocation of forkhead transcription factor/DAF-16. Proc Natl Acad Sci USA. 2005; 102: 4494-9). Age-dependent increased JNK activity is sufficient to overcome AKT inhibition of FOXO factors and causes FOXO factors to activate their targeted genes (Greer, E L and Brunet, A. FOXO transcription factors at the interface between longevity and tumor suppression. Oncogene. 2005; 24: 7410-25).

Senescence attenuates the HSR/HSF1 axis with some level of compensation by the DAF-16/FOXO pathway, as shown in FIG. 9. Activation of DAF16/FOXO during aging produces high molecular weight protein aggregates that are not degraded, but secreted to the extracellular space (Cohen, E, Bieschke, J, Perciavalle, R M, Kelly, J W and Dillin, A. Opposing activities protect against age-onset proteotoxicity. Science. 2006; 313: 1604-10). This process resembles amyloid plaque formation in Alzheimer's disease. In fact, recent evidence indicates that amyloid aggregation can be prevented by the over-expression of HSF1, thus reducing the proteotoxicity of aging (Cohen, E, Bieschke, J, Perciavalle, R M, Kelly, J W and Dillin, A. Opposing activities protect against age-onset proteotoxicity. Science. 2006; 313: 1604-10). Therefore, HSR/HSF1 pathway attenuation is intimately linked to abnormal protein accumulation and cell degeneration. Abnormal protein accumulation is noted in multiple age-related diseases such as Alzheimer's disease, Parkinson's disease, Frontotemporal dementia, and Diffuse Lewy Body dementia. Similarly, diabetes mellitus is another acquired disease that expresses multiple abnormal proteins such as Amidori or age glycosylation end (AGE) products. In the vascular system CADASIL (cerebral autosomal dominant arteriopathy with subcortical infarcts and leukoencephalopathy) is produced due to accumulation of the abnormal protein Notch 3 (Joutel, A, Andreux, F, Gaulis, S, Domenga, V, Cecillon, M, Battail, N, Piga, N, Chapon, F, Godfrain, C and Tournier-Lasserve, E. The ectodomain of the Notch3 receptor accumulates within the cerebrovasculature of CADASIL patients. J Clin Invest. 2000; 105: 597-605). Also, there are more examples of protein deposition in other important organs (heart, kidneys and liver) (Liu, Z and Barrett, E J. Human protein metabolism: its measurement and regulation. Am J Physiol Endocrinol Metab. 2002; 283: E1105-12).

Given the age-dependent decline in countering proteotoxicty, preservation or enhancement of the heat-shock response during senescence is a highly desirable goal. Modulation of the HSR and chaperones provides protection in a variety of pathophysiologic states important to elderly such as ischemia/reperfusion, inflammation/sepsis, and neurodegenerative diseases (Hay, D G, Sathasivam, K, Tobaben, S, Stahl, B, Marber, M, Mestril, R, Mahal, A, Smith, D L, Woodman, B and Bates, G P. Progressive decrease in chaperone protein levels in a mouse model of Huntington's disease and induction of stress proteins as a therapeutic approach. Hum Mol Genet. 2004; 13: 1389-405; Snoeckx, L H, Cornelussen, R N, Van Nieuwenhoven, F A, Reneman, R S and Van Der Vusse, G J. Heat shock proteins and cardiovascular pathophysiology. Physiol Rev. 2001; 81: 1461-97; Stefani, M and Dobson, C M. Protein aggregation and aggregate toxicity: new insights into protein folding, misfolding diseases and biological evolution. J Mol Med. 2003; 81: 678-99; Van Molle, W, Wielockx, B, Mahieu, T, Takada, M, Taniguchi, T, Sekikawa, K and Libert, C. HSP70 protects against TNF-induced lethal inflammatory shock. Immunity. 2002; 16: 685-95).

Chaperone induction has been proven in preclinical studies to be an efficient therapeutic approach in cardiovascular and age-related degenerative diseases involving cancer, diabetes, and neurodegeneration (DeFranco, D B, Ho, L, Falke, E and Callaway, C W. Small molecule activators of the heat shock response and neuroprotection from stroke. Curr Atheroscler Rep. 2004; 6: 295-300; Soti, C, Nagy, E, Giricz, Z, Vigh, L, Csermely, P and Ferdinandy, P. Heat shock proteins as emerging therapeutic targets. Br J Pharmacol. 2005; 146: 769-80). Besides physiologic stressors (exercise, sauna, calorie restriction), both synthetic and plant-derived small molecules are among promising lead compounds that enhance the HSR/HSF1 pathway (Auluck, P K and Bonini, N M. Pharmacological prevention of Parkinson disease in *Drosophila*. Nat Med. 2002; 8: 1185-6; Ikeyama, S, Kusumoto, K, Miyake, H, Rokutan, K and Tashiro, S. A non-toxic heat shock protein 70 inducer, geranylgeranylacetone, suppresses apoptosis of cultured rat hepatocytes caused by hydrogen peroxide and ethanol. J Hepatol. 2001; 35: 53-61; Jurivich, D A, Sistonen, L, Kroes, R A and Morimoto, R I. Effect of sodium salicylate on the human heat shock response. Science. 1992; 255: 1243-5; Kieran, D, Kalmar, B, Dick, J R, Riddoch-Contreras, J, Burnstock, G and Greensmith, L. Treatment with arimoclomol, a coinducer of heat shock proteins, delays disease progression in ALS mice. Nat Med. 2004; 10: 402-5; Siemann, E H and Creasy, L L. Concentration of the Phytoalexin Resveratrol in Wine. Am J Enol Viticult. 1992; 43: 49-52; Vigh, L, Literati, P N, Horvath, I, Torok, Z, Balogh, G, Glatz, A, Kovacs, E, Boros, I, Ferdinandy, P, Farkas, B, Jaszlits, L, Jednakovits, A, Koranyi, L and Maresca, B. Bimoclomol: a nontoxic, hydroxylamine derivative with stress protein-inducing activity and cytoprotective effects. Nat Med. 1997; 3: 1150-4).

As previously disclosed above and in accordance one or more embodiments with the present invention, electromagnetic fields may be utilized to provide regulatory effects on HSR/HSF1. Specifically, serial exposure of aging cells to long wave, low intensity EMF enhances the HSR/HSF-1 pathway and augments chaperone induction during stress (see also Perez, F P, Zhou, X, Morisaki, J and Jurivich, D. Electromagnetic field therapy delays cellular senescence and death by enhancement of the heat shock response. Exp Gerontol. 2008; 43: 307-16). It has been found that REMFS does not induce a classical heat shock response at 37° C. as evidenced by lack of HSF1-DNA binding activity that is normally induced after a 40 to 42° C. heat shock for several minutes. Id. Furthermore, REMFS does not cause a measurable increase in cell culture temperature, thus negating the possibility that its biological effects are due to cellular responses to thermal injury. As shown above, novel REMFS therapy primes the heat shock response at several nodes of activation. For instance, novel applications of REMFS may disrupt the HSF1-Hsp90 complex, releasing Hsp90 and thereby pre-conditioning HSF1 for subsequent stresses (see FIG. 11). Furthermore, REMFS may increase HSF1 phosphorylation, and enhances HSF1-DNA binding, both which likely explain why HSP70 expression improves during stress.

Overall, one or more novel applications of REMFS may achieve several biological effects that delay the aging process. REMFS extends the total number of population doublings of young and old mouse fibroblasts and contributes to the reversal to a youthful morphology of cells at the end of their replicative lifespan. REMFS therapy stimulates rejuvenating effects as evidenced by delay and reversal in phenotypic cellular changes associated with senescence, possible due to enhancement of the HSR/HSF1 pathway which increases degradation of protein aggregates associated to age-related pathology. One possible mechanism by which REMFS affects HSF1 is that it acts as a catalyst that changes redox state; this idea takes into account that aging may inhibit HSR through intra-molecular disulfide cross-linkage of ox-HSF1 (Manalo, D J and Liu, A Y. Resolution, detection, and characterization of redox conformers of human HSF1. J Biol Chem. 2001; 276: 23554-61). Another possible mechanism is that REMFS resets the age-dependent molecular brake on HSF1 and thereby rejuvenates its DNA binding and transcriptional activities (de la Hoz, A, Diaz-Ortiz, A and Moreno, A. Microwaves in organic synthesis. Thermal and non-thermal microwave effects. Chem Soc Rev. 2005; 34: 164-78).

Another observation made herein is that REMFS either prolongs the replicative capacity of serially passaged cells or pulls cells out of the G1/S interface of the cell cycle. It has been observed that REMFS transiently reverses the loss of proliferative capacity in senescent cells; the mechanism of this phenomenon is unknown, one possible explanation would be activation of an "alternative lengthening of telomeres" (ALT) in which chaperones are involved in telomere repair (Henson, J D, Neumann, A A, Yeager, T R and Reddel, R R. Alternative lengthening of telomeres in mammalian cells. Oncogene. 2002; 21: 598-610; Kroll, J. The molecular chaperones and the phenomena of cellular immortalization and apoptosis in vitro. Ann N Y Acad Sci. 2004; 1019: 568-71).

All these beneficial effects of REMFS are achieved without causing malignant transformation in the cells treated with REMFS therapy. Ultimately and importantly, REMFS enhances cellular defenses of human T cells as reflected in lower cell mortality during severe stress when compared to non-treated T cells.

An aspect of REMFS therapy is its potential to promote repair of cellular damage caused by the aging process. This process is believed to be a key to strategies for engineered negligible senescence. Important attributes include, counteracting cell loss, protein and telomere damage, death-resistance under stress, and increased protein repair and degradation to prevent the accumulation of intra and extracellular junk. All these REMFS effects can minimize cellular damage over time and thus delay or retard any age-related pathology. In addition to REMFS therapy, consideration can be given to synergistic therapies that selectively improve HSR/HSF1 and DAF-16/FOXO pathways. For example, DAF-16/FOXO activating agents such as Resveratrol do not delay or reverse cellular senescence, (Stefani, M, Markus, M A, Lin, R C, Pinese, M, Dawes, I W and Morris, B J. The effect of resveratrol on a cell model of human aging. Ann N Y Acad Sci. 2007; 1114: 407-18), but a combination therapy with both Reservatrol and REMFS may provide greater beneficial effect on cellular senescence than either treatment alone. In thinking about engineered negligible senescence, one may wish to promote the DAF-16/FOXO pathway as a means to prevent oxidative stress while simultaneously enhance the HSF/HSF1 pathway so as to repair all the residual protein damage caused by oxidative stress that could not be prevented by the antioxidant systems.

Biophysical Model

Although the biological effects of low-frequency electromagnetic radiation have been studied since the time of Paracelsus [circa 1500], lack of consensus exists whether these effects are therapeutically significant. In addition, many EMF studies have not been replicated successfully (Robertson J A, Thomas A W, Bureau Y, Prato F S. The influence of extremely low frequency magnetic fields on cytoprotection and repair. Bioelectromagnetics, 2007; 28:16-30). These variances may occur because different EMF doses are likely to have varying effects on molecules and compounds. This phenomenon may be due to unmeasured factors, such as free radical production and direct protein damage, which can activate the HSR. The fact that EMF therapy does not uniformly elevate HSPs is believed to be not particularly relevant within the context of the present disclosure. REMFS therapy alone did not increase HSPs levels, but increased expression of HSPs when cells were stressed by heat shock treatments compared to non-REMFS exposed cells.

As previously disclosed herein, not all EMF are harmful to life. Some are neutral and others beneficial. As disclosed herein, low dose EMF (50 MHz/0.5 W) has been shown to stimulate non-thermal cell stress as a pathway for improved cellular longevity and protection (see also Perez, F P, Zhou, X, Morisaki, J and Jurivich, D. Electromagnetic field therapy delays cellular senescence and death by enhancement of the heat shock response. Exp Gerontol. 2008; 43: 307-16).

The technology of applying certain beneficial EMF to the body to stimulate the natural stress response and upregulate the repair and maintenance systems is a potentially new form of therapy. Medical interventions that involve the therapeutic application of extremely low-level EMF signals have been identified. They stimulate therapeutic effects such as osteogenesis, soft tissue regeneration, psychophysiological modulations, and immune system enhancement (Sentman, D D. Schumann resonances. Volland H (ed.) Handbook of Atmospheric Electrodynamics. 1995; 1: 267-295); Siskin, B F and Walker, J. Therapeutic aspects of electromagnetic fields for soft-tissue healing. Electromagnetic Fields: Biological Interactions and Mechanisms. Advances in Chemistry Series 250. 1995; 277-285). Another more widely used application is pulsed electromagnetic stimulation at 7 Hz, useful to promote bone tissue regeneration (Sharrard, W J. A double-blind trial of pulsed electromagnetic fields for delayed union of tibial fractures. J Bone Joint Surg Br. 1990; 72: 347-55). This noninvasive treatment for bone fractures has been FDA approved for over 20 years. These and other bioelectromagnetic medical applications are in various states of development, acceptance, and use around the globe. Many of the therapeutic signals have been identified as natural frequencies of the body, and they are typically in the ELF (extremely low frequency) range less than 100 Hz. Siskin and Walker (see Siskin, B F and Walker, J. Therapeutic aspects of electromagnetic fields for soft-tissue healing. Electromagnetic Fields: Biological Interactions and Mechanisms. Advances in Chemistry Series 250. 1995; 277-285) have reviewed the healing effects of specific frequency windows, and some of them are as follows: 2 Hz, nerve regeneration; 10 Hz, ligament healing; 15, 20, and 72 Hz, stimulation of capillary formation and fibroblast proliferation.

Prior to the present invention, there had been no consensus on whether EMF effects are therapeutically significant. The present invention demonstrates that REMFS therapy enhances HSF1/HSR pathway and provides a potential mechanistic explanation for its beneficial effects (see Perez, F P, Zhou, X, Morisaki, J and Jurivich, D. Electromagnetic field therapy delays cellular senescence and death by enhancement of the heat shock response. Exp Gerontol. 2008; 43: 307-16). The data disclosed herein indicates that REMFS therapy can delay cellular senescence and death by enhancement of the heat shock pathway. This observation opens new therapeutic possibilities for interventions on protein-associated and age-related diseases. Interestingly, some ELF activates directly— after the application of ELF there is an increased expression of HSPs. On the other hand the application of REMFS does not activate the HSR directly and does not increase expression of HSR. REMFS pre-conditions HSR and over expressed HSPs only after a subsequent stress (heat shock) compared to non-REMFS-treated cells.

Electromagnetic Field Exposures.

Electromagnetic field (EMF) consists of waves of electric and magnetic energy moving together (i.e., radiating) through space at the speed of light. Taken together, all forms of electromagnetic energy are referred to as the electromagnetic "spectrum." Engineered negligible senescence through REMFS therapy utilizes 50 MHz which belongs to the radio frequency part of EMF spectrum. The radio frequency (RF) part of the electromagnetic spectrum is generally defined as that part of the spectrum where electromagnetic waves have frequencies in the range of about 3 kilohertz (3 kHz) to 300 gigahertz (300 GHz). The energy levels associated with RF are not great enough to cause the ionization of atoms and molecules and RF energy is, therefore, a type of non-ionizing radiation. "Ionization" is a process by which electrons are stripped from atoms and molecules. This process can produce molecular changes that can lead to damage in biological tissue, including effects on DNA, the genetic material.

As disclosed herein in accordance with certain embodiments, the EMF exposures (irradiation) that provide beneficial effects and are appropriate for human size were perform at 50 MHz and a power of 0.5 W. These experiments have been carried out using a transverse electromagnetic (TEM) chamber. A TEM chamber is an expanded coaxial transmission line operating in the TEM mode, the fundamental mode of propagation in the structure. TEM chambers can be used to simulate free-space, near field, and grounded conditions (Michaelson, S M and Lin, J C. Biological Effects and Health Implications of Radiofrequency Radiation. 1987). In previous experiments, we obtained the free-space or plane wave irradiation condition by terminating the chamber in its characteristic impedance (50 ohms). The chamber has a rectangular metallic section containing a flat-metal-strip center conductor located between the top and bottom of the chamber, which is used for sample placement. The wave impedance inside the chamber is very close to the intrinsic impedance of free space (Baird, R C. Methods of calibrating microwave hazard meters. Biological Effects and Health Hazards of Microwave Radiation. 1974; pp. 228-36). The absolute electric field strength E at the center of the cell is linearly polarized and is given by the equation (Michaelson, S M and Lin, J C. Biological Effects and Health Implications of Radiofrequency Radiation. 1987):

$$E = \frac{(PR)^{1/2}}{d}$$

where P is the net power delivered to the cell, R=50 ohms, and d is the distance between the center and the top or bottom of the chamber. The corresponding power density is $$P_a = \frac{E^2}{2\eta}$$

where $\eta$ is the wave impedance inside the chamber (ideally 377 ohms). The field or power density in the plane midway between the center conducting strip and the cell wall is fairly uniform and the introduction of the cell culture into the chamber alters the field distribution slightly (Baird, R C. Methods of calibrating microwave hazard meters. Biological Effects and Health Hazards of Microwave Radiation. 1974; pp. 228-36; Lin, J C, Nelson, J C and Ekstrom, M E. Effects of Repeated Exposure to 148-Mhz Radio-Waves on Growth and Hematology of Mice. Radio Sci. 1979; 14: 173-179).

Any organ that shows functional decline, such as the brain, kidneys, joints, liver, or heart may benefit from engineered REMFS to engage beneficial effects from the enhancement of the HSR/HSF1 pathway. This approach will be valuable in treating age-related diseases in humans such as heart failure, osteoarthritis, chronic kidney disease, COPD and neurodegenerative diseases. Enhanced specificity may prove an important method for mitigating side effects and for increasing tolerance to therapy. For example, cardiac age-related diseases are the result of increased afterload which causes myocyte hypertrophy, resulting in accelerated cell death and heart failure. Engineered REMFS will prevent and delay this cellular hypertrophy and cell death; therefore, preventing or delaying heart disease.

Aging is characterized by reduction in the structure and function of cells, tissues and organs. Human aging attenuates the most important repair and maintenance cellular system, the HSR/HSF1 pathway, causing age-related protein accumulation and cellular senescence. REMFS therapy enhances and prevents the age-related decline of HSR/HSF1 pathway and regulates cellular senescence. As disclosed herein, engineered REMFS therapy for manipulating age-related diseases in humans may be possible. Studies using short-lived invertebrates offer the best possibility to rapidly identify and characterize REMFS treatments that have strong effects on longevity and protein accumulation. The enhancement of the HSR/HSF1 pathway confers the most dramatic effects to date on beta amyloid accumulation in C. elegans. Studies can be performed in transgenic mouse model such as AD and other age-related diseases to determine the effects on each disease and the organism in general. Clinical trials for preventing and treating age-related diseases in humans such as heart failure, chronic kidney disease, osteoarthritis, COPD and neurodegenerative diseases can be performed in accordance with the present disclosure. Considering that REMFS may have a significant effect on protein aggregation and toxicity; the application of this therapy in Alzheimer's disease, Parkinson's disease, Fronto-temporal dementia, and other protein associated diseases is contemplated. Bioengineering techniques can be used to calculate the right dose (wavelength, frequency and power) for different tissues and organs that the EMF will pass before reaches its goal.

The biogerontologist Aubrey de Grey proposed Strategies for Engineered Negligible Senescence [SENS] in the Annals of the New York Academy of Sciences. The application of Engineered REMFS Therapy is consistent with de Grey's principles (de Grey A. Biogerontologists' duty to discuss timescales publicly, Annals NY Acad Sci 2004; 1019:542-45) and may have important clinical implications not only in age-related protein associated diseases but also in reversing cellular senescence in aging cells, preventing cell and mass loss characteristic of the aging process. In addition, Engineered REMFS Therapy in consort with other therapeutic agents that affect longevity pathways such as Resveratrol may offer multiplicative deterrents to age-related pathology in humans. In accordance with the present invention, REMFS therapy delays cellular senescence by preconditioning of the HSR/HSF1 pathway.

It will be apparent to persons skilled in the art that various modifications and alterations to the preferred embodiments mentioned above may be made without departing from the underlying concept of the inventions. All such modifications and alterations are included within the scope of the present invention.

We claim:

1. A method comprising:
applying repetitive radio frequency electromagnetic field shock to at least one living cell, wherein the repetitive radio frequency electromagnetic field shock is configured to precondition improvement in either heat shock factor 1 (HSF1) or heat shock response (HSR) function, or HSF1 and HSR function, and increasing expression of heat shock proteins (HSPs) without increasing temperature or causing external heat damage, wherein the precondition improvement is characterized in an increase in HSF1-heat shock element (HSE) binding.

2. The method of claim 1, wherein the applying of the repetitive radio frequency electromagnetic field shock is configured to disrupt the molecular brake of HSF1-DNA binding without resulting in a decline of Hsp90.

3. The method of claim 1, wherein the applying repetitive radio frequency electromagnetic field shock is at about 50 MHz/0.5 W continuous radiation.

4. The method of claim 1, wherein the applying repetitive radio frequency electromagnetic shock is between about 5 minutes to about 30 minutes in duration and is repeated for a period selected from the group consisting of: once a day, about once every two days, about once every three days, about once a week, and about twice a week.

5. The method of claim 1, wherein the applying repetitive radio frequency electromagnetic field shock delays or reverses senescence.

6. The method of claim 5, wherein the at least one living cell is a plurality of T-cells and at least a portion of the applying repetitive radio frequency electromagnetic field shock is applied to the T-cells during IL-2 stimulation.

7. The method of claim 5, wherein at least a portion of the application of the repetitive radio frequency electromagnetic field shock is applied concurrently with a treatment that augments the DAF-16 (FOXO) pathway.

8. The method of claim 1, wherein the repetitive radio frequency electromagnetic field shock is applied to the at least one cell until the cell reaches cellular senescence to delay at least one aging characteristic.

9. The method of claim 8, wherein the at least one aging characteristic is a decline in cell proliferation rates or terminal lifespan or senescent phenotype.

10. The method of claim 1, wherein the at least one cell is a T cell.

11. The method of claim 1, wherein the at least one living cell is a plurality of living cells, and the method further comprises applying repetitive radio frequency electromagnetic field shock to a plurality of in vivo living cells.

12. The method of claim 11, wherein the in vivo living cells are brain cells.

13. The method of claim 1, wherein the repetitive radio frequency electromagnetic field shock is delivered to at least a localized region of the body of a patient.

14. The method of claim 1, wherein the repetitive radio frequency electromagnetic field shock is provided by a transversal electromagnetic chamber.

15. The method of claim 1, wherein the at least one living cell is a plurality of living cells and the applying repetitive radio frequency electromagnetic field shock extends the replicative lifespan of the at least one living cell.

16. The method of claim 15, wherein the applying repetitive radio frequency electromagnetic field shock extends the terminal lifespan of at least one living cell of the plurality of living cells.

17. The method of claim 1, wherein the at least one living cell is a plurality of living fibroblast cells and the applying repetitive radio frequency electromagnetic field shock delays the average age-related enlargement and diversification of at least one fibroblast cell.

18. The method of claim 1, wherein the at least one living cell is a plurality of living fibroblast cells and the applying repetitive radio frequency electromagnetic field shock reverts at least one fibroblast cell to a more youthful phenotype.

19. The method of claim 1, wherein the applying repetitive radio frequency electromagnetic field shock to the at least one living cell treats at least one age related disease.

20. The method of claim 19, wherein the at least one age related disease is Alzheimer's disease.

21. A method comprising:
applying repetitive radio frequency electromagnetic field shock to at least one living cell, wherein the repetitive radio frequency electromagnetic field shock is configured to precondition enhancement of the heat shock response (HSR)/heat shock factor 1 (HSF1) pathway and augment chaperone induction during stress, and increasing expression of heat shock proteins (HSPs) without increasing temperature or causing external heat damage wherein the precondition enhancement is characterized in an increase of HSF1-heat shock element (HSE) binding.

22. The method of claim 21, wherein the applying of the repetitive radio frequency electromagnetic field shock is configured to disrupt the molecular brake of HSF1-DNA binding without resulting in a decline of Hsp90.

23. The method of claim 21, wherein the applying repetitive radio frequency electromagnetic field shock is at about 50 MHz/0.5 W continuous radiation.

* * * * *